US007208628B2

(12) United States Patent
Todd et al.

(10) Patent No.: US 7,208,628 B2
(45) Date of Patent: Apr. 24, 2007

(54) COMPOSITIONS AND METHODS FOR THE TREATMENT OF HEPATITIS C VIRUS INFECTION

(75) Inventors: Scott C. Todd, Manhattan, KS (US); Paul W. Baures, Manhattan, KS (US)

(73) Assignee: Kansas State University Research Foundation, Manhattan, KS (US)

(*) Notice: Subject to any disclaimer, the term of this patent is extended or adjusted under 35 U.S.C. 154(b) by 477 days.

(21) Appl. No.: 10/144,294

(22) Filed: May 13, 2002

(65) Prior Publication Data

US 2003/0219893 A1 Nov. 27, 2003

(51) Int. Cl.
*A61K 31/215* (2006.01)
*A01N 37/30* (2006.01)

(52) U.S. Cl. ...................................... 564/123; 514/616

(58) Field of Classification Search ................. 514/396
See application file for complete search history.

(56) References Cited

U.S. PATENT DOCUMENTS

| | | | | |
|---|---|---|---|---|
| 4,552,891 | A | 11/1985 | Ho et al. | 514/443 |
| 5,393,773 | A | 2/1995 | Craig et al. | 514/415 |
| 5,554,639 | A | 9/1996 | Craig et al. | 514/415 |
| 5,801,161 | A | 9/1998 | Merkus | 514/52 |
| 5,864,037 | A | 1/1999 | Chasin et al. | 544/118 |
| 5,869,479 | A | 2/1999 | Kreutner et al. | 514/212 |

OTHER PUBLICATIONS

Wagner, C.E. "Synthesis of 1-Boraadamantaneamine Derivatives with Selective Astrocyte vs C6 Glioma Antiproliferative Activity. A Novel Class of Anti-Hepatitis Agents with Potential to Bind CD81" J. Med. Chem (2003) vol. 46, pp. 2823-2833.*

Chen, H. "Acyclic Nucleoside/Nucleotide Analogues With an Imidazole Ring Skeleton" Nucleos. Nucleot. & Nucliec Acids (2001 vol. 20, No. 8, pp. 1599-1614.*

Aleksandrova, I. Ya., et al., "Investigation of the Conformations of the Diamides of Imidazole- and Pyrazoledicarboxylic Acids," *Zh. Org. Khim.* 12:1109-1115, 1976.

Allander, T., et al., "Hepatitis C Virus Envelope Protein E2 Binds to CD81 of Tamarins," *Virology* 277:358-367, 2000.

Baures, P.W., et al., "Directed Intermolecular Association by Complementary Molecular Edges in 6-Methoxycoumarin," *Crystal Growth & Design* 2(2): 107-110, 2002.

Baures, P.W. "Heterocyclic HIV-1 Protease Inhibitors," *Organic Letters* 1:249-252, 1999.

Baures, P.W., et al., "Hydrogen Bonding Isosteres: Bimolecular Carboxylic Acid and Amine-N-oxcide Interactions Mediated Via CH . . . O Hydrogen Bonds," *Bioorganic & Medicinal Chemistry* 8: 1599-1605, 2000.

Clark, K. et al., "PGRL Is a Major CD81-Associated Protein on Lymphocytes and Distinguishes a New Family of Cell Surface Proteins," *The Journal of Immunology* 167:5115-5121, 2001.

Cochran, A., "Antagonists of protein—protein interactions," *Chemistry & Biology* 7:R85-R94, 2000.

Hadlock, K.G., et al., "Human Monoclonal Antibodies that Inhibit Binding of Hepatitis C Virus E2 Protein to CD81 and Recognize Conserved Conformational Epitopes," *J. Virol.* 74:10407-10416, 2000.

Higginbottom, A., et al., "Identification of Amino Acid Residues in CD81 Critical for Interaction with Hepatitus C Virus Envelope Glycoprotein E2," *J. Virol.* 74:3642-3649, 2000.

Janin, J. "Kinetics and Thermodynamics of Protein—Protein Interactions," in *Protein—Protein Recognition Kleanthous*, C., Ed., 2000, pp. 1-32, Oxford University Press, Oxford.

Jones, S. and Thornton, J.M. "Analysis and Classification of Protein—Protein Interactions from a Structural Perspective" in *Protein—Protein Recognition*, Kleanthous, C., Ed., 2000, pp. 33-59, Oxford University Press, Oxford.

Kitadokoro, K., et al., "CD81 Extracellular Domain 3D Structure: Insight Into the Tetraspanin Superfamily Structural Motifs," *EMBO J.* 20:12-18, 2001.

Levy, S., et al., "CD81 (TAPA-1): A Molecule Involved in Signal Transduction and Cell Adhesion in the Immune System," *Annu. Rev. Immunol.* 16:89-109, 1998.

Ma, B., et al., "Protein Functional Epitopes: Hot Spots, Dynamics and Combinatorial Libraries," *Curr. Opin. Struct. Biol.* 11:364-369, 2001.

Maecker, H.T., et al., "The Tetraspanin Family: Molecular Facilitators," *FASEB J.* 11:428-442, 1997.

McCormick, F., "Small-molecule inhibitors of cell signaling," *Current Opinion in Biotechnology* 11:593-597, 2000.

Michnick, S.W. "Exploring Protein Interactions by Interaction-Induced Folding of proteins from Complementary Peptide Fragments," *Curr. Opin. Struct. Biol.* 11:472-477, 2001.

Petracca, R., et al., "Structure-Function Analysis of Hepatitis C Virus Envelope-CD81 Binding," *J. Virol.* 74:4824-4830, 2000.

Pileri, et al., "Binding of Hepatitis C Virus to CD81," *Science* 282:938-941, 1998.

Qin, J., et al., "Protein—Protein Interactions Probed by Nuclear Magnetic Resonance Spectroscopy," *Methods Enzymol.* 339:377-389, 2001.

Teichmann, S.A., et al., "Determination of Protein Function, Evolution, and Interactions by Structural Genomics," *Curr. Opin. Struct. Biol.* 11:354-363, 2001.

Todd, S. C., et al., "Sequences and Expression of Six New Members of the Tetraspanin/TMASF Family," *Biochim Ciophys Acta* 1399:101-104, 1998.

VanCompernolle, S.E., et al., "Anti-CD81 activates LFA-1 on T cells and promotes T cell-B cell collaboration," *Eur. J. Immunol.* 31:823-831, 2001.

Wang, W., et al., "Biomolecular Simulations: Recent Developments in Force Fields, Simulations of Enzyme Catalysis, Protein-Ligand, Protein—Protein, and Protein-Nucleic Acid Noncovalent Interactions," *Annu. Rev. Biophys. Biomol. Struct.* 30:211-243, 2001.

(Continued)

*Primary Examiner*—Bruce R. Campell
*Assistant Examiner*—Michelle Horning
(74) *Attorney, Agent, or Firm*—Medlen & Carroll, LLP

(57) ABSTRACT

This invention relates to methods and compositions directed towards the diagnosis and treatment of Hepatitis C virus infection and the screening of potential therapeutic compounds using novel small molecules based on imidazole-4, 5-dicarboxylic acids scaffolds.

3 Claims, 8 Drawing Sheets

OTHER PUBLICATIONS

Wright, M.D. and Tomlinson, M.G. "The Ins and Outs of the Transmembrane 4 Superfamily," *Immunol. Today* 15:588-594, 1994.

Wünschmann, et al., "Characterization of Hepatitis C Virus (HCV) and HCV E2 Interactions with CD81 and the Low-Density Lipoprotein Receptor," *J. Virology* 74:10055-10062, 2000.

Yasuda, N. et al., "Intramolecular Hydrogen Bonding in Imidazole-4(5)-alkoxycarbonyl-5(4)-carboxamide Derivatives," *J. Het. Chem.* 24:303-307, 1987.

Zutshi, R., et al., "Inhibiting the assembly of protein—protein interfaces," *Current Opinion In Chemical Biology* 2:62-66, 1998.

* cited by examiner a)

b)

c)

JR-1-74; R = (*S*)-PheO *t*Bu
JR-1-95; R = (*S*)-PheOMe
JR-1-81; R = (*S*)-LeuOMe
JR-1-84; R = (*S*)-ValOMe
JR-1-91; R = (*S*)-AlaOMe
JR-1-99; R = GlyO *t*Bu
JR-1-131; R = GlyOEt

3; JR-1-132 R = (*S*)-PheO *t*Bu
4; JR-1-133 R = (*S*)-IleO*t*Bu
5; JR-1-220 R = (*S*)-ValOBzl
AL-2-257; R = (*S*)-ValOEt
AL-2-259; R = (*S*)-ValO*t*Bu
AL-2-239; R = (*S*)-LeuOBzl

Figure 7 (cont.)

8 AL-2-125 BzlO - Val - NHCO - Im - 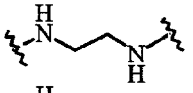 - Im - CONH - Val - OBzl

9 AL-2-127 BzlO - Val - NHCO - Im - 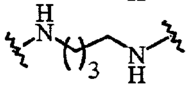 - Im - CONH - Val - OBzl

AL-2-128 BzlO - Val - NHCO - Im - 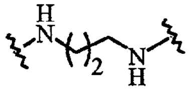 - Im - CONH - Val - OBzl

AL-2-130 BzlO - Val - NHCO - Im - 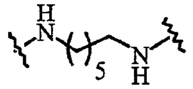 - Im - CONH - Val - OBzl

6 AL-2-132 *t*BuO - Phe - NHCO - Im - - Im - CONH - Phe - O*t*Bu

AL-2-136 BzlO - Val - NHCO - Im - 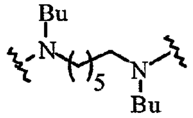 - Im - CONH - Val - OBzl

AL-2-140 BzlO - Val - NHCO - Im - 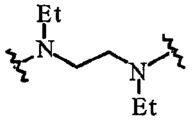 - Im - CONH - Val - OBzl.

AL-2-255 BzlO - Leu - NHCO - Im - - Im - CONH - Leu - OBzl

AL-2-261 *t*BuO - Val - NHCO - Im - - Im - CONH - Val - O*t*Bu

AL-2-263 EtO - Val - NHCO - Im - - Im - CONH - Val - OEt

AL-2-269 $HO_2C$ - Leu - NHCO - Im - - Im - CONH - Leu - $CO_2H$

AL-2-222 BzlO - Val - NHCO - Im - 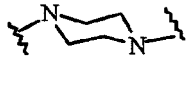 - Im - CONH - Val - OBzl

AL-2-243 BzlO - Val - NHCO - Im -  - Im - CONH - Val - OBzl

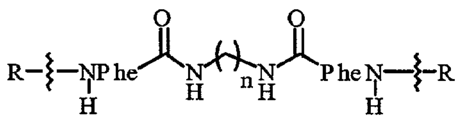

10 JR-1-124, n = 2, R = Boc
11 JR-1-137, n = 3, R = Boc
12 JR-1-144, n = 4, R = Boc

13 JR-1-155a *t*BuO - Phe - NHCO - Im - n = 2 - Im - CONH - Phe - O*t*Bu

14 JR-1-155b *t*BuO - Phe - NHCO - Im - n = 3 - Im - CONH - Phe - O*t*Bu

16 JR-1-152 *t*BuO - Ile - NHCO - Im - n = 2 - Im - CONH - Ile - O*t*Bu

17 JR-1-154 *t*BuO - Ile - NHCO - Im - n = 4 - Im - CONH - Ile - O*t*Bu

COMPOSITIONS AND METHODS FOR THE TREATMENT OF HEPATITIS C VIRUS INFECTION

This invention was developed with funding from the NIH-COBRE program under grant #1P20RR015563-01. The government may have certain rights in this invention.

FIELD OF THE INVENTION

This invention relates to compounds and methods for the screening of compounds effective for the treatment of Hepatitis C virus infection. In one embodiment, the compounds for the effective treatment of Hepatitis C virus are proteomimetics based on imidazole-4,5-dicarboxylic acid scaffolds.

BACKGROUND

Hepatitis C virus (HCV) infection is the most common chronic blood-borne infection in the United States. The Center for Disease Control (CDC) estimates that during the 1980's, an average of 230,000 new infections occurred each year. The CDC also estimates that the prevalence of HCV in the U.S. will triple between now and the year 2010.

HCV is one of the most important causes of chronic liver disease in the United States. It accounts for about 20 percent of acute viral hepatitis, 60 to 70 percent of chronic hepatitis, and 30 percent of cirrhosis, end-stage liver disease, and liver cancer. Almost 4 million Americans, or 1.8 percent of the U.S. population, have antibody to HCV (anti-HCV), indicating ongoing or previous infection with the virus. Hepatitis C causes an estimated 8,000 to 10,000 deaths annually in the United States.

Chronic hepatitis C can cause cirrhosis, liver failure, and liver cancer. About 20 percent of patients develop cirrhosis within 10 to 20 years of the onset of infection. Liver failure from chronic hepatitis C is one of the most common reasons for liver transplants in the United States. Hepatitis C might be the most common cause of primary liver cancer in the developed world. In Italy, Spain, and Japan, at least half of liver cancers could be related to HCV. Males, alcoholics, patients with cirrhosis, people over age 40, and those infected for 20 to 40 years are more likely to develop HCV-related liver cancer.

Chronic hepatitis C varies greatly in its course and outcome. At one end of the spectrum are patients who have no signs or symptoms of liver disease and completely normal levels of serum liver enzymes. Liver biopsy usually shows some degree of chronic hepatitis, but the degree of injury is usually mild, and the overall prognosis may be good. At the other end of the spectrum are patients with severe hepatitis C who have symptoms, HCV RNA in serum, and elevated serum liver enzymes, and who ultimately develop cirrhosis and end-stage liver disease. In the middle of the spectrum are many patients who have few or no symptoms, mild to moderate elevations in liver enzymes, and an uncertain prognosis.

Currently in the United States, two different regimens have been approved as therapy for hepatitis C: Monotherapy with alpha interferon and combination therapy with alpha interferon and ribavirin. Combination therapy consistently yields higher rates of sustained response than does monotherapy. Both methods of treatment have multiple side effects. Additionally, few options exist for patients who either do not respond to therapy or who respond and later relapse. Combination treatment is more expensive and is associated with more side effects than monotherapy, but, in most situations, it is preferable. Even for patients that do respond, the side effects may be intolerable.

As is evident from the foregoing, new medications and approaches to the treatment of HCV are needed.

SUMMARY OF THE INVENTION

This invention relates to methods and compositions directed towards the diagnosis, screening and treatment of Hepatitis C virus infection using novel small molecules based on imidazole-4,5-dicarboxylic acid (I45DC) scaffolds.

Although the present invention is not limited to any particular theory, the empirically discovered I45DC scaffolds employed herein for therapeutic and screening applications represent both novel scaffolds as well as an unexplored approach in scaffold design: namely, the use of non-covalent forces in water to predictably control the presentation of the pharmacological functional groups appended to the scaffold backbone.

Although the present invention is not limited to any particular theory or mechanism, the approach used here to inhibit protein-protein interactions involves the development of scaffolds that present chemical diversity in the form of either amino acids or other chemical structures or both and, thereby, result in sufficiently large surfaces that are capable of disrupting protein-protein interactions such as the binding of CD81 with HCV-E2. HCV-E2 is a coat protein of the Hepatitis C virus. CD81 (cluster of differentiation marker 81) is a surface protein that binds the E2 coat protein of the HCV. CD81 and HCV-E2 are binding partners.

Although the present invention is not limited to any particular theory or mechanism, an advantage of the I45DC scaffold-based compounds of the present invention is that they permit the combining of state-of-the-art elements in drug design: namely, combinatorial methods for the discovery and evolution of molecules as well as structure-based information for directing library development. The I45DC scaffolds are, from a manufacturing standpoint, relatively simple to prepare, have predictable conformations and are amphiphilic in order to aid solubility in both water as well as non-polar environments such as membranes. In one embodiment, the present invention contemplates the use of I45DC scaffold-based HCV-E2/CD81 binding inhibitors for the therapeutic treatment of HCV infection. In another embodiment, the present invention contemplates HCV-E2/CD81 binding inhibitors that are comprised of at least one I45DC molecule. In yet another embodiment, the present invention contemplates an I45DC scaffold that comprises from two to ten I45DC molecules. In still yet another embodiment, the present invention contemplates HCV-E2/CD81 binding inhibitors that comprise from two to five I45DC molecules.

In one embodiment, the present invention contemplates side chains bound to the I45DC scaffold. The invention is not limited to any particular type of side chain. In another embodiment, the side chains comprise amino acids and amino acid-based molecules. In yet another embodiment, the side chains comprise phenylalanine-derivitized diamines. The present invention is not limited to any particular number of side chains on the I45DC scaffold. The relative number of side chains will generally correlate with the number of I45DC molecules in the scaffold. In one embodiment, the I45DC scaffold comprises at least one side chain. In another embodiment, the I45DC scaffold comprises from two to twenty side chains. In yet another embodiment, the I45DC scaffold comprises from three to ten side chains. In still yet another embodiment, the side chains are derived from N,N'-diethylethylenediamine.

The present invention contemplates methods and compositions for the treatment of Hepatitis C viral infections. In one embodiment, the present invention contemplates the treatment of a human exhibiting symptoms of HCV infection by the administration of a therapeutic amount of an I45DC scaffold-based compound of the present invention. In another embodiment, the therapeutic amount of an I45DC scaffold-based compound is administered until at least one of the HCV symptoms is reduced. In yet another embodiment, the present invention contemplates the therapeutic amount of an I45DC scaffold-based compound of the present invention is administered in combination with a pharmaceutically acceptable carrier. In still yet another embodiment, the therapeutic amount of an I45DC scaffold-based compound of the present invention is administered in combination with excipients. The present invention is not limited by the nature of the excipients used. Excipients may be, for example, fillers, binders, colors, flavors, agents to adjust pH or osmolarity, dilutants and agents added to aid ease of manufacture.

The present invention is not limited by the mode of administration. For example, in one embodiment, the present invention contemplates the method of administration of the therapeutic amount of an I45DC scaffold-based compound by intravenous injection, subcutaneous injection, intramuscular injection, oral administration (e.g., tablets, capsules, liquids, etc.), topical administration and sublingual, buccal and nasal administration.

In embodiments of the present invention it is contemplated that the compounds of the present invention are administered along with physiologically acceptable carriers. Among the physiologically acceptable carriers for use in the present invention are, for example, physiological saline or phosphate buffered saline. Such a physiologically acceptable carrier can also include a non-irritant preservative, such as, e.g., benzalkonium chloride at 0.05% (w/v) to 0.02% (w/v).

I45DC scaffold-based compounds and pharmaceutical compositions comprising an I45DC scaffold-based compound may also be administered intranasally. Formulations suitable for intranasal administration include ointments, creams, lotions, pastes, gels, sprays, aerosols, oils and other pharmaceutical carriers which accomplish direct contact between an I45DC scaffold-based compound or a pharmaceutical composition comprising an I45DC scaffold-based compound and the nasal cavity. Examples of pharmaceutical compositions administered intranasally are described in U.S. Pat. Nos. 5,393,773 and 5,554,639 to Craig et al.; and U.S. Pat. No. 5,801,161 to Merkus, all hereby incorporated by reference.

I45DC scaffold-based compounds and pharmaceutical compositions comprising an I45DC scaffold-based compound may also be administered through respiratory inhalation. Formulations suitable for respiratory inhalation include ointments, creams, lotions, pastes, gels, sprays, aerosols, oils and other pharmaceutical carriers which accomplish direct contact between an I45DC scaffold-based compound or a pharmaceutical composition comprising an I45DC scaffold-based compound and the respiratory tract. Examples of pharmaceutical compositions administered through respiratory inhalation are described in U.S. Pat. No. 4,552,891 to Hu et al.; U.S. Pat. No. 5,869,479 to Kreutner et al., and U.S. Pat. No. 5,864,037 to Chasis et al., all incorporated herein by reference.

In some embodiments, intranasal administration and respiratory inhalation are the preferred modes of administration due to the ease of administration and faster onset of therapeutic activity when compared to oral administration. It is contemplated that intranasal administration and respiratory inhalation are advantageous as they may allow a smaller effective dosage to be administered than would be possible with the oral route of administration. A mode of administration comprises administration to the lung. In a preferred mode, intrapulmonary delivery of pharmacologic agents to patients can be accomplished via aerosolization. Alternatively, the agent may be administered to the lung through a bronchoscope.

In other embodiments, intravenous administration is preferred. It is contemplated that intravenous administration of an I45DC scaffold-based therapeutic compound would allow the fastest onset of therapeutic administration allowing for smaller doses to be used.

In one embodiment, the present invention contemplates a compound comprising an imidazole-4,5-dicarboxylic acid scaffold that at least partially inhibits the interaction (e.g., binding) of HCV-E2 and CD81. In another embodiment, the present invention contemplates a compound comprising an imidazole-4,5-dicarboxylic acid scaffold in linked combination with N,N'-diethylethylenediamine. In yet another embodiment, the present invention contemplates the I45DC scaffold-based compound inhibits the interaction of HCV and CD81. In still yet another embodiment, the present invention contemplates the I45DC scaffold-based compound has an $EC_{50}$ value of between approximately 0.1 μM and 1000 μM. In still yet another embodiment, the present invention contemplates the I45DC scaffold-based compound has an $EC_{50}$ value of between approximately 1.0 μM and 250 μM.

In one embodiment, the present invention contemplates a method of treating HCV infection comprising a) providing, i) a human with one or more symptoms of HCV infection and, ii) an I45DC scaffold-based compound and; b) administering said compound until at least one of said symptoms is reduced. In one embodiment, the present invention contemplates a method of treating HCV infection wherein, reduction in symptoms is measured by detection of HCV infection by a diagnostic assay. In yet another embodiment, the present invention contemplates the I45DC scaffold-based compound of the present invention further comprises a pharmaceutically acceptable carrier.

In one embodiment, the present invention contemplates a method, comprising; a) providing, i) cells expressing CD81, ii) a substance suspected of at least partially inhibiting the binding of HCV-E2 to CD81, iii) at least a portion of recombinant HCV-E2 and, iv) a detection means; b) contacting said cells with said substance to produce treated cells; c) contacting said treated cells with recombinant HCV-E2 to produce bound recombinant HCV-E2, and; d) detecting said bound recombinant HCV-E2 with said detection means. The present invention is not limited to any particular detection means. In one embodiment, the present invention contemplates that the detection means is selected from a group comprising of flow cytometry, immunohistochemistry and detection of radioactive tags. In another embodiment, the present invention contemplates that the portion of recombinant HCV-E2 comprises the amino acids Ala384-Lys715. In still yet another embodiment, the present invention contemplates that the portion of recombinant HCV-E2 is expressed on the surface of a cell. In still yet another embodiment, the present invention contemplates that the CD81 expressing cells are T cells. In still yet another embodiment, the present invention contemplates that the T cells are Molt4 cells. In still yet another embodiment, it is contemplated that the expressed HCV-E2 binds to CD81 on the surface of a cell.

DEFINITIONS

Figure 1:
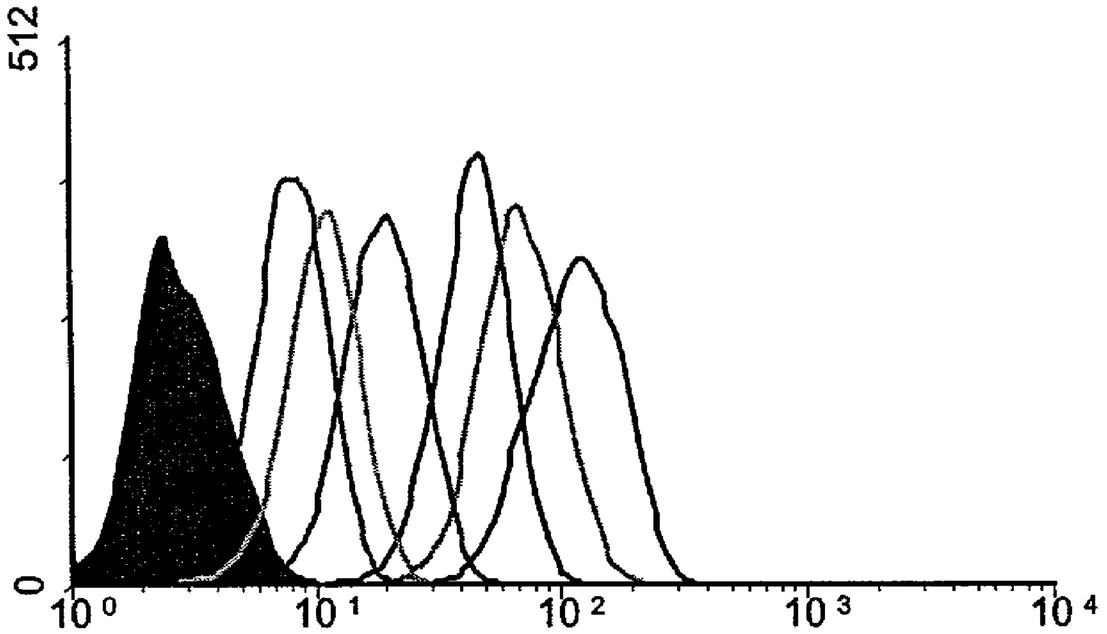
FIG. 1 shows the binding of HCV-E2 to Molt4 T cells. Cells were incubated with 10, 5, 2.5, 1.25, 0.6 or 0.3 μg/mL E2 for 30 min. at 37° C. prior to washing and detection with saturating amounts of mAb 6F6 and goat anti-mouse Alexa 488. The right-most histogram represents the 10 μg/mL concentration and each successive histogram moving leftward represents a 1:2 dilution of the E2. The solid histogram represents no E2.

To facilitate understanding of the invention, a number of terms are defined below.

As used herein, the term "purified", "purifying" or "to purify" refers to the removal of one or more (undesired) components from a sample. For example, where recombinant polypeptides are expressed in bacterial host cells, the polypeptides are purified by the removal of host cell proteins thereby increasing the percent of recombinant polypeptides in the sample. Likewise, I45DC scaffold-based compounds of the present invention are purified from reaction constituents. In the context of the present invention, purity is measured by $^{1}H$ and $^{13}C$ NMR spectroscopic data consistent with structure and is denoted as "percent yield." In the context of the present invention a purified component, e.g., an I45DC scaffold-based compound or scaffold precursor, may comprise from 1% to 90% of the mixture. In a preferred embodiment, the purified compound may comprise from 10% to 99% of the reaction mixture.

As used herein, the term "substantially purified" refers to molecules that are isolated or separated from the reaction mixture and are at least 50% free, preferably 75% free and more preferably 90% free from other components with which they are associated.

The term "compound" refers to any chemical entity, pharmaceutical, drug, and the like that may or may not be used be used to treat or prevent a disease, illness, sickness, or disorder of bodily function. "Therapeutic compounds" comprise both known and potential therapeutic compounds. A compound can be determined to be potentially therapeutic by testing using the testing methods of the present invention. A "known therapeutic compound" refers to a compound that has been shown (e.g., through animal trials or prior experience with administration to humans) to be effective in such treatment or prevention.

A compound is said to be "in a form suitable for administration such that the compound is bio-available in the blood of the animal" when the compound may be administered to an animal by any desired route (e.g., oral, intravenous, subcutaneous, intrathecal, intraperitoneal, intramuscular, etc.) and the compound or its active metabolites appears in the blood of the animal in an active form.

As used herein, "pharmaceutically acceptable carrier" herein shall refer to a composition, liquid or solid, generally recognized as useful for the administration of therapeutics to humans and other animals.

As used herein, the phrases "pharmaceutically acceptable salts", "a pharmaceutically acceptable salt thereof" or "pharmaceutically accepted complex" for the purposes of this application are equivalent and refer to derivatives prepared from pharmaceutically acceptable non-toxic acids or bases including inorganic acids and bases and organic acids and bases. Since the compound of the present invention is basic, salts may be prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, palmoic, pantothenic, phosphoric, succinic, sulfuric, tartaric acid, p-toluenesulfonic, and the like. Preferred acid addition salts are the chloride and sulfate salts.

"Patient" shall be defined as a human or other animal, such as a farm animal or lab animal (e.g., guinea pig or mouse and the like), that may be in need of alleviation or amelioration from a recognized medical condition.

As used herein, "by oral administration" refers to the introduction of a pharmaceutical composition into a subject by way of the oral cavity (e.g. in aqueous liquid or solid form).

As used herein, "cutaneously" refers to the introduction of a pharmaceutical composition into a subject by application to the surface of the skin such that the composition is absorbed into the subject.

As used herein, "intranasally" refers to the introduction of a pharmaceutical composition within the nasal cavity.

As used herein, "respiratory inhalation" refers to the introduction of a pharmaceutical composition within the respiratory tract.

A "cell-targeting mechanism" refers to a process, procedure or reagent that allows a compound or reagent (e.g. an I45DC scaffold-based compound of the present invention) to locate to a cell or cells in an organism. The targeting need not be absolute. The targeting need not be specific for a particular type of cell. An example of a targeting mechanism is a peptide or other compound that may be recognized by a cell surface receptor so that, if in proximity to the cell surface receptor, the peptide or other compound will be bound by the cell surface receptor, and, thereby, be localized or targeted to the cell displaying the cell surface receptor, thereby also targeting the bound I45DC scaffold-based compounds to the cell.

"Transformation" refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects. Additionally, transformation refers to cells that have been transformed naturally, usually through genetic mutation. Furthermore, transformation refers to cell lines which have become "immortal" (i.e., capable of indefinite growth in culture) due to, e.g., mutations (nature or otherwise) in the genetic makeup of the cells. In the present invention, Molt4 cells are transformed cells.

"Detection means" herein shall refer to a method or procedure used to quantify or qualify the results of, for example, a diagnostic assay. Examples of detection means are flow cytometry, immunohistochemistry, detection of radioactive tags or markers, etc. A detection means may also be, for example, visual observation of the patient and the use of customary medical diagnostic tools such as thermometers and stethoscopes. Alexa-488 is a fluorochrome useful in the detection of labeled targets via immunohistochemical means.

"Flow cytometry" herein shall refer to a method or procedure by which samples, for example blood cells and antibodies, can be separated, classified and quantitated. In flow cytometry a monocellular stream of cells, platelets or other microscopic particulate elements are passed through a beam of laser light. The cells are categorized first by size and then computer analyzed to sort the mixture of cellular elements into cell type by size. Cells may also be labeled with fluorescent dye and then passed, in suspending medium, through a narrow dropping nozzle so that each cell is in a small droplet. A laser based detector system is used to excite bound fluorescent tags and droplets with positively fluorescent cells are given an electric charge. Charged and uncharged droplets may be separated as they fall between charged plates and so collect in different tubes. Additionally, flow cytometry can be used to quantify the number of bound molecules per cell. The fluorescence intensity of a cell correlates with the number of detecting molecules specifically bound to its surface. "Mean fluorescence intensity" (MFI) is an average of this number over a large population or analyzed cells.

The flow cytometer can be used either as an analytical tool, as a cell counter counting the number of labelled cells in a population or to separate populations of the cells based on selected characteristics. Further sophistication can be built into the system by using a second laser system at right angles to the first to look at a second fluorescent label or to gauge cell size on the basis of light scatter. The system looks at large numbers of individual cells and makes possible the separation of populations with, for example: particular surface properties.

Tabulation of counted data in conjunction with size analysis enables determination of relative percentages of each specific cellular subset for which monoclonal antibody conjugates are utilized, even when the size of the cell is identical to other subset species.

"Immunohistochemistry" shall refer to the histochemical localization of immunoreactive substances using labeled antibodies as reagents.

"Imidazole-4,5-dicarboxylic acid" herein shall refer to a chemical of the structure below.

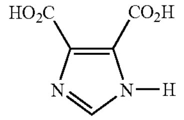

"I45DC scaffold" or "oligometric I45DC" herein shall refer to a compound wherein, more than one I45DC molecules are linked by, for example, chemical bonds. In one embodiment of the invention, the I45DC scaffold comprises one I45DC molecule. In another embodiment, two I45DC molecules are linked to make a scaffold. In yet another embodiment, three I45DC molecules are linked to make a scaffold. In still yet another embodiment, four or more I45DC molecules are linked to make a scaffold.

Symptoms are "reduced" when there is a detectable quantitative reduction. For example, fever and/or respiration rate can be quantitatively detected and measured and thus a reduction in fever and/or respiration can be readily detected and quantitated. Similarly, fluid loss is detectable and can be measured. It is not intended that the present invention be limited to precise levels or reductions of a particular magnitude. Most importantly, the present invention is not limited to "cures" or complete elimination of each and every symptom. It is sufficient that there is a reduction in one or more symptoms, regardless of the magnitude of the reduction. If the magnitude of reduction is not complete then the symptom is said to be "partially reduced" or "partially inhibited." In this regard, "at least partially inhibits" shall refer to a situation where, e.g., the symptom of a disease is reduced up to and including the elimination of the symptom as determined by conventional means of detection and measurement of the symptom.

"Partially inhibit", in regards to the HCV-E2/CD81 interaction, refers to a situation wherein the measurable detection of HCV-E2/CD81 binding is reduced as a result of, e.g., addition of a compound suspected of inhibiting the HCV-E2/CD81 interaction, as compared to the situation wherein said compound is not added. "Partially inhibit" means any measurable inhibition not including total measurable inhibition. "At least partially inhibits" is any measurable inhibition including total measurable inhibition.

"Interaction", in regards to HCV-E2/CD81 interaction, refers to the binding of HCV-E2 with CD81. The binding interaction of HCV-E2/CD81 may be reversible or irreversible.

"Pyrazines" are nitrogen-based heterocyclic molecules. I45DC-based compounds are a pyrazines.

"In linked combination", "in linked combination with", "in operable combination", "in operable order" and "operably linked" as used herein refer to the linkage of molecules (e.g., compounds) in such a manner that a new molecule is produced.

"Receptor" herein shall refer to a molecular structure (e.g. a protein) within a cell or on the surface of the cell characterized by selective binding of a specific substance or substances (e.g., a ligand).

"Ligand" herein shall refer to a molecule (e.g., a protein, or proteomimic) that binds to another molecule. For example, a soluble molecule such as a hormone or neurotransmitter that binds to a receptor.

"HCV-E2", "Hepatitis C virus-E2" and "E2" herein shall refer to a coat protein of the Hepatitis C virus. HCV-E2 and CD81 are binding partners.

"CD81" and "Cluster of Differentiation marker 81" herein shall refer to a cell (e.g., a human T cell) surface protein that binds the E2 coat protein of the HCV. CD81 and HCV-E2 are binding partners.

"N,N'-diethylethylenediamine" herein shall refer to the chemical structure below.

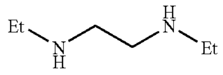

"$IC_{50}$" and "Inhibitory concentration 50%" shall both refer to the concentration of an inhibitor required to inhibit the receptor binding affinity of a ligand by 50%. The $IC_{50}$ is usually measured with a competitive binding curve. "$EC_{50}$" and Effective concentration 50%" shall both refer to the concentration of a drug that gives 50% of a maximum response. It is used to measure the potency of a drug. A low $EC_{50}$ means, relatively, a high potency.

"Diagnostic assay" or "assay" herein shall refer to a procedure or method for the determination of, for example, the amount of a particular constituent of a mixture or of the biological or pharmacological potency of a drug.

GENERAL DESCRIPTION OF THE INVENTION

This invention relates to methods and compositions directed towards the diagnosis and treatment of Hepatitis C virus infection and the screening of potential therapeutic compounds using novel small molecules based on imidazole-4,5-dicarboxylic acids scaffolds.

The Hepatitis C virus (HCV) is a positive-stranded RNA virus which is the causal agent for chronic liver infection afflicting more than 170,000,000 people world-wide. Once infected, 75% of these individuals will fail to clear the virus and will remain infected for the rest of their lives and 10–20% will develop cirrhosis or cancer. Although the virus was discovered in 1989, development of anti-viral therapeutics has been hampered by lack of reliable cell culture systems or animal models to study the virus. The current treatment for HCV infection is alpha-interferon in combination with ribavirin which has only modest success rates and significant side effects. Alpha-interferon sales exceeded $1.3 billion dollars in 2000.

Currently in the United States, two different regimens have been approved as therapy for hepatitis C: Monotherapy with alpha interferon and combination therapy with alpha interferon and ribavirin. Combination therapy consistently yields higher rates of sustained response than monotherapy. Combination treatment is more expensive and is associated with more side effects than monotherapy, but, in most situations, it is preferable. At present, interferon monotherapy should be reserved for patients who have contraindications to the use of ribavirin.

Common side effects of alpha interferon (occurring in more than 10 percent of patients) include: fatigue, muscle aches, headaches, nausea and vomiting, skin irritation at the injection site, low-grade fever, weight loss, irritability, depression, mild bone marrow suppression and reversible hair loss. The most common side effects of ribavirin are: anemia, fatigue and irritability, itching, skin rash, nasal stuffiness, sinusitis, and cough. Ribavirin causes a dose-related hemolysis of red cells; with combination therapy, hemoglobin usually decreases by 2 to 3 g/dL and the hematocrit by 5 to 10 percent. The amount of decrease in hemoglobin is highly variable. The decrease starts between weeks 1 and 4 of therapy and can be precipitous. Some patients develop symptoms of anemia, including fatigue, shortness of breath, palpitations, and headache.

Uncommon side effects of alpha interferon and combination therapy (occurring in less than 2 percent of patients) include: autoimmune disease (especially thyroid disease), severe bacterial infections, marked thrombocytopenia, marked neutropenia, seizures, depression and suicidal ideation or attempts, retinopathy (microhemorrhages), hearing loss and tinnitus. Rare side effects include acute congestive heart failure, renal failure, vision loss, pulmonary fibrosis or pneumonitis, and sepsis. Deaths have been reported from acute myocardial infarction, stroke, suicide, and sepsis.

One method for inhibiting viral infection is to prevent the virus from ever entering the cell in the first place. HCV has two proteins in its envelope, E1 and E2, which it may use to bind to and enter cells. Recently a research group at Chiron Inc. (Pileri, P., et al., "Binding of Hepatitis C Virus to CD81" *Science* 282:938–94, 1998) reported that CD81 is a cellular receptor for HCV-E2. The interaction of human CD81 with the HCV-E2 protein is believed to be important in the infectivity of HCV. Additionally, it was found that binding of HCV-E2 to CD81 on cells of the immune system (T cells) alters T cell function and may be a way in which HCV evades and manipulates immune responses thereby allowing it to persist in the patient for many years.

I. Protein-Protein Binding Interactions

The ever increasing understanding of protein-protein interactions comes in part from advances in structural biology, including X-ray crystallography (Jones, S. and Thornton, J. M. "Analysis and Classification of Protein-Protein Interactions from a Structural Perspective" in Protein-Protein Recognition, Kleanthous, C., Ed., 2000, pp. 33–59, Oxford University Press, Oxford.), NMR spectroscopy (Qin, J., et al., "Protein-Protein Interactions Probed by Nuclear Magnetic Resonance Spectroscopy" *Methods Enzymol.* 339: 377–389, 2001), and theoretical calculations on proteins (Wang, W., et al., "Biomolecular Simulations: Recent Developments in Force Fields, Simulations of Enzyme Catalysis, Protein-Ligand, Protein-Protein, and Protein-Nucleic Acid Noncovalent Interactions" *Annu. Rev. Biophys. Biomol. Struct.* 30:211–243, 2001), as well as from improvements in protein biochemistry (Michnick, S. W. "Exploring Protein Interactions by Interaction-Induced Folding of proteins from Complementary Peptide Fragments" *Curr. Opin. Struct. Biol.* 11:472–477, 2001; Teichmann, S. A., et al., "Determination of Protein Function, Evolution, and Interactions by Structural Genomics" *Curr. Opin. Struct. Biol.* 11:354–363, 2001) including advances such as improved protein expression systems, site-directed mutagenesis techniques, and accurate thermodynamic measurements on purified proteins (Janin, J. "Kinetics and Thermodynamics of Protein-Protein Interactions" in Protein-Protein Recognition, Kleanthous, C., Ed., 2000, pp. 1–32, Oxford University Press, Oxford.). The resulting data and corresponding interpretations have highlighted the requirements that face any effort aimed to disrupt protein-protein interactions. It is important to note that protein-protein interactions are subject to the same factors governing any chemical process including kinetics, thermodynamics, concentration of the proteins, the environmental context of the interaction, temperature, and even the time course of the overall binding event. (Janin, J. "Kinetics and Thermodynamics of Protein-Protein Interactions" in Protein-Protein Recognition, Kleanthous, C., Ed., 2000, pp. 1–32, Oxford University Press, Oxford; Ma, B., et al., "Protein Functional Epitopes: Hot Spots, Dynamics and Combinatorial Libraries" *Curr. Opin. Struct. Biol.* 11:364–369, 2001). In addition, protein-protein interfaces do not solely bury hydrophobic surfaces, as polar residues are also found in interfacial "hot spots." (Ma, B., et al., "Protein Functional Epitopes: Hot Spots, Dynamics and Combinatorial Libraries" *Curr. Opin. Struct. Biol.* 11:364–369, 2001). It is true that protein surfaces showing a higher than average amount of non-polar residues will largely be involved in buried protein-protein interfaces, but this fact does not preclude the formation of interfaces that also contain polar groups. Furthermore, proteins involved in signal transduction generally bury a large amount of surface area (=550 Å$^2$ per protein) when interacting with other proteins. (Janin, J. "Kinetics and Thermodynamics of Protein-Protein Interactions" in Protein-Protein Recognition, Kleanthous, C., Ed., 2000, pp. 1–32, Oxford University Press, Oxford) It may seem obvious that these complexed surfaces are geometrically and electrostatically complementary to one another; yet, some proteins are shown to be quite plastic and capable of varying their interface conformation to coincide with the interaction. (Ma, B., et al., "Protein Functional Epitopes: Hot Spots, Dynamics and Combinatorial Libraries" *Curr. Opin. Struct. Biol.* 11:364–369, 2001)

II Structure of CD81

Figure 3:
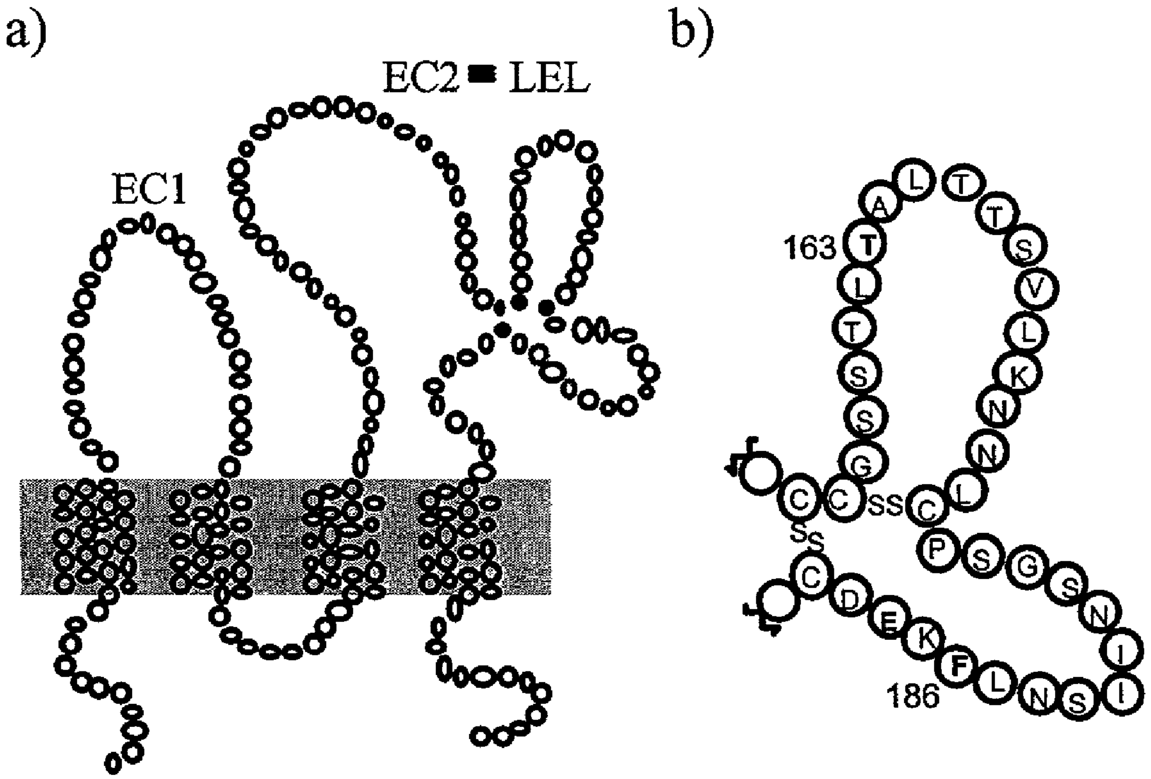
FIGS. 3A and 3B. (A) shows a schematic illustration of the structure of the tetraspanin family of proteins. (B) shows an expanded view of the hypervariable region (HVR) within the second extracellular loop, EC2 (LEL, large extracellular loop). Amino acids T163 and F186 are known to influence the binding of HCV-E2.

CD81 is a tetraspanin. The tetraspanin family of cell surface molecules play a role in regulating cell adhesion, migration and survival. (Levy, S., et al., "CD81 (TAPA-1): A Molecule Involved in Signal Transduction and Cell Adhesion in the Immune System" *Annu. Rev. Immunol.* 16:89–109, 1998). The tetraspanin family includes at least twenty members. (Todd, S. C., et al., "Sequences and Expression of Six New Members of the Tetraspanin/TM4SF Family" *Biochim Biophys Acta* 1399:101–104, 1998). Tetraspanins are expressed in every metazoan from flies and nematodes to humans. Tetraspanins possess four transmembrane domains that come together to form two extracellular loops, EC1 and EC2 (also called LEL), of roughly 30 and 110 amino acids respectively (FIG. 3).

Figure 4:
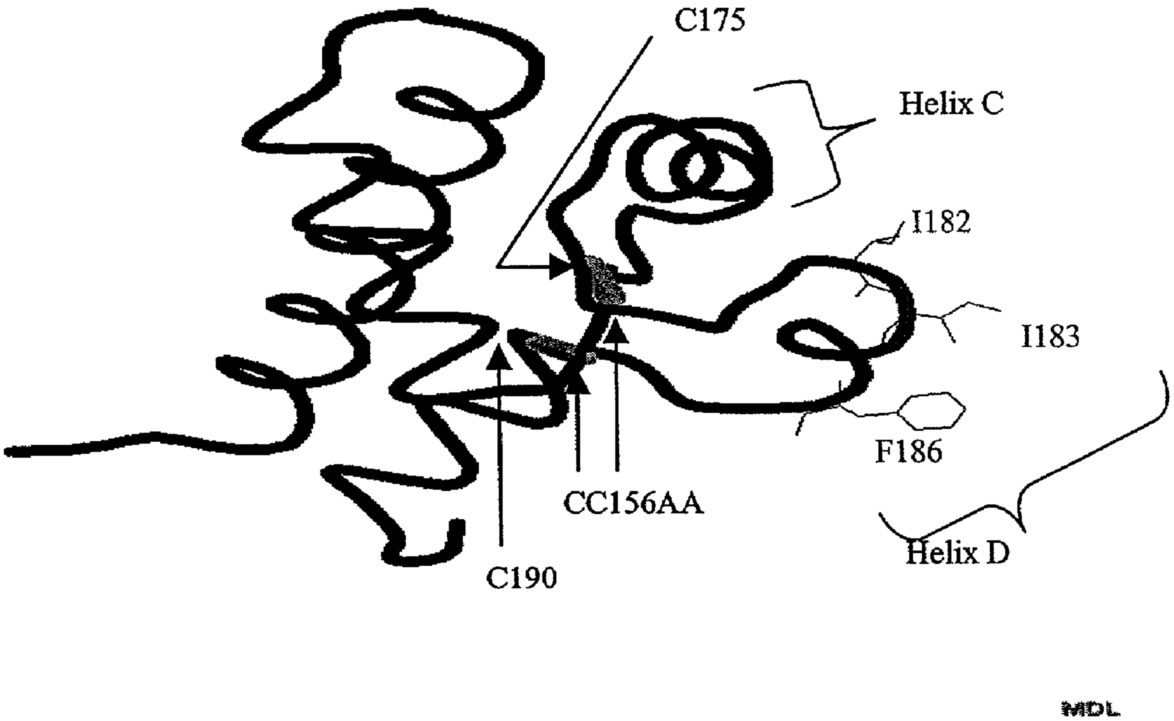
FIG. 4 shows the X-ray crystal structure of CD81-EC2. Backbone structure of the second extracellular loop of CD81 with selected side chains in helix D shown in the putative region of HCV-E2 binding.

Both the N- and C-termini face the cytoplasm and these cytoplasmic "tails" are fairly short (generally<15 amino acids each). In addition to this basic structure, members of the family maintain charged residues within the transmembrane domains and position-specific cysteines in EC2. (Maecker, H. T., et al., "The Tetraspanin Family: Molecular Facilitators" *FASEB J.* 11:428–442, 1997; Wright, M. D. and Tomlinson, M. G. "The Ins and Outs of the Transmembrane 4 Superfamily" *Immunol. Today* 15:588–594, 1994). For CD81, the cysteines in EC2 were hypothesized to form a disulfide bond that constrains the structure and isolates a divergent loop (Levy, S., et al., "CD81 (TAPA-1): A Molecule Involved in Signal Transduction and Cell Adhesion in the Immune System" *Annu. Rev. Immunol.* 16:89–109, 1998), a theory now supported by the available structural data. (Kitadokoro, K., et al., "CD81 Extracellular Domain 3D Structure: Insight Into the Tetraspanin Superfamily Structural Motifs" *EMBO J.* 20:12–18, 2001). The divergent loop in CD81 is comprised of two helical regions termed helix C and helix D which are a primary target for small molecule intervention in the protein-protein interaction with HCV-E2 (FIG. 4).

III. CD81-LEL X-Ray Structure

An X-ray crystal structure of the second extracellular loop (EC2) of CD81 has confirmed the disulfide bonds formed between the four conserved cysteine residues as well as providing valuable information regarding the structure of the loops in the hypervariable region (HVR). (Kitadokoro, K., et al., "CD81 Extracellular Domain 3D Structure: Insight Into the Tetraspanin Superfamily Structural Motifs" *EMBO J.* 20:12–18, 2001). The EC2 contains several alpha-helices, including helix C and helix D which are formed by the amino acids between the two disulfide bridges (FIG. 4). Although these helices are not particularly long, they do pack against one another and expose the side chains of both Thr163 and Phe186 to the solvent. Thus, attention is focused on this region of CD81 as that potentially responsible for the binding interaction with HCV-E2 and thereby providing a logical target for directing our research efforts.

IV. CD81 and HCV-E2 Binding Interaction

The binding interaction between human CD81 and the hepatitis C E2 glycoprotein (HCV-E2) has been examined by several labs in addition to our own. (Pileri, P., et al. "Binding of Hepatitis C Virus to CD81" *Science* 282:938–941, 1998; Higginbottom, A., et al., "Identification of Amino Acid Residues in CD81 Critical for Interaction with Hepatitis C Virus Envelope Glycoprotein E2" *J. Virol.* 74:3642–3649, 2000; Petracca, R., et al., "Structure-Function Analysis of Hepatitis C Virus Envelope-CD81 Binding" *J. Virol.* 74:4824–4830, 2000; Wunschmann, S., et al., "Characterization of Hepatitis C Virus (HCV) and HCV E2 Interactions with CD81 and the Low-Density Lipoprotein Receptor" *J. Virol.* 74:10055–10062, 2000; Hadlock, K. G., et al. "Human Monoclonal Antibodies That Inhibit Binding of Hepatitis C Virus E2 Protein to CD81 and Recognize Conserved Conformational Epitopes" *J. Virol.* 74:10407–10416, 2000).

Sequence alignments between the human and the African green monkey (AGM) CD81 offer clues regarding the requirements for CD81 to act as a receptor for HCV infection, of which the AGM does not suffer. (Higginbottom, A., et al., "Identification of Amino Acid Residues in CD81 Critical for Interaction with Hepatitis C Virus Envelope Glycoprotein E2" *J. Virol.* 74:3642–3649, 2000). Site-directed mutagenesis has highlighted two residues in CD81 that impact the binding interaction with HCV-E2. (Higginbottom, A., et al., "Identification of Amino Acid Residues in CD81 Critical for Interaction with Hepatitis C Virus Envelope Glycoprotein E2" *J. Virol.* 74:3642–3649, 2000). One of these critical residues is Phe186 which, when mutated to a Leucine residue, is reported to not bind effectively to HCV-E2.

DESCRIPTION OF THE PREFERRED EMBODIMENTS

This invention relates to methods and compositions directed towards the diagnosis and treatment of Hepatitis C virus infection and the screening of potential therapeutic compounds using novel small molecules based on imidazole-4,5-dicarboxylic acids scaffolds.

Although the present invention is not limited to any particular theory, the empirically discovered I45DC scaffolds employed herein for therapeutic, diagnostic and screening applications represent both novel scaffolds as well as an unexplored approach in I45DC scaffold design: namely, the use of non-covalent forces in water to predictably control the presentation of the pharmacophoric functional groups appended to the scaffold backbone.

Although the present invention is not limited to any particular theory or mechanism, the approach used here to inhibit protein-protein interactions involves the development of scaffolds that present chemical diversity in the form of either amino acids or other chemical structures or both and, thereby, result in sufficiently large surfaces that are capable of disrupting protein-protein interactions such as the CD81 with HCV-E2 binding. Approaches to the discovery of antibodies and protein-based inhibitors of HCV-E2 and CD81 binding have been published. (Pileri, P., et al., "Binding of Hepatitis C Virus to CD81" *Science* 282:938–94, 1998; Higginbottom, A., et al, "Identification of Amino Acid Residues in CD81 Critical for Interaction with Hepatitis C Virus Envelope Glycoprotein E2" *J. Virol.* 74:3642–3649, 2000). These approaches often have limited practical application because the inhibitors show low avidity or are subject to in vivo degradation. Both of these problems would necessitate large dosing regimes in order for the reagents to be effective as therapeutics, thus, potentially leading to adverse side effects.

An advantage of the I45DC scaffold-based compounds of the present invention is that they permit the combining of state-of-the-art elements in drug design: namely, combinatorial methods for the discovery and optimization of inhibitory molecules well as structure-based information (predictable conformations) for directing library development. The I45DC scaffolds are, from a manufacturing stand point, relatively simple to prepare, have predictable conformations and are amphiphilic in order to aid solubility in both water as well as membranes. In one embodiment, the present invention contemplates the use of I45DC-based HCV-E2/CD81 binding inhibitors for the therapeutic treatment of HCV infection.

In one embodiment, the present invention contemplates a cell culture system in which to measure the binding of HCV-E2 to human CD81 on living T cells. CD81 sequence information in non-human species (which are not susceptible to HCV) along with crystal structure data for CD81 has been used to focus on a region of CD81 which is considered likely to be the site where HCV-E2 binds. Based on the structural modeling a series of molecules have been designed which may mimic the target region of CD81. These CD81-mimics have been tested for their ability to bind to HCV-E2 and thereby block the interaction of the viral envelope protein E2 with its cellular receptor.

Several I45DCs contemplated by the present invention block binding of HCV-E2 to CD81. The results from experiments that use monomeric and oligomeric N,N'-disubstituted imidazole-4,5-dicarboxylic acid (I45DC's) for their ability to block binding of HCV-E2 to CD81 expressed on human T cells are outlined in the Experimental section. Although the present invention is not limited to any particular $IC_{50}$ value, the best inhibitor to date has an approximate $IC_{50}$ value of 45 μM in this assay and contains two I45DCs linked through a short diaminoalkane bridge (Scheme 6; compound 19). The present invention also contemplates that further variation of this structure will improve its affinity and solubility characteristics. Compound 19 represents both a therapeutic compound and a lead drug for the treatment of HCV infection.

Identifying new scaffolds and general methods for small molecule scaffold development is an important goal in bio-organic and medicinal chemistry research. The empirically discovered I45DC scaffolds employed herein for the discovery of CD81 mimics represent both novel scaffolds as well as an unexplored approach in I45DC scaffold design: namely, the use of non-covalent forces in water to predictably control the presentation of the pharmacophoric functional groups appended to the scaffold backbone.

Although the present invention is not limited to any particular theory, it is believed that important factors control the ability of I45DCs to form intramolecularly hydrogen bonded conformations. Certain structural modifications can affect intramolecular hydrogen bond strength and conformation by altered resonance stabilization between the hydrogen bonded carbonyl group and the imidazole ring. (Yasuda, N. et al., "Intramolecular Hydrogen Bonding in Imidazole-4(5)-alkoxycarbonyl-5(4)-carboxamide Derivatives" *J. Het. Chem.* 24:303–307, 1987; Aleksandrova, I. Ya., et al., "Investigation of the Conformations of the Diamides of Imidazole- and Pyrazoledicarboxylic Acids" *Zh. Org. Khim.* 12:1109–1115, 1976). These known structural data provide important data regarding the impact of structural changes on the hydrogen bond strength in the scaffolds developed as well as the environments likely to enhance hydrogen bond formation in the scaffolds developed and described in the present invention. Additional work has demonstrated that hydrogen bonded conformation is reliable even in an aqueous medium such as plasma.

From X-ray crystallography data on the I45DCs, the similar distance between the two substituents on the imidazole as compared with the C(alpha)-C(alpha) distance (6.3 A) between adjacent side chains on the same face of an ideal alpha-helix was demonstrated. The Ca-Ca distance between adjacent side chains is 3.8 Å. Mimicry of the four hydrophobic side chains in the CD81 helix D, three of which are shown in FIG. 4, was considered possible by linking a symmetric and dissymmetric I45DC through the imidazole ring C2 position or nitrogens. As an alternative design strategy and for the purposes of obtaining preliminary results validating our hypothesis, we connected two I45DCs through diamine linkers either with or without amino acid residues included. These compounds were tested in the CD81 with HCV-E2 binding assay.

Experimental

The following examples serve to illustrate certain preferred embodiments and aspects of the present invention and are not to be construed as limiting the scope thereof.

In the experimental disclosure which follows, the following abbreviations apply: I45DC, (imidazole-4,5-dicarboxamide); mM, (millimolar); Å, (angstrom); $IC_{50}$, inhibitory concentration 50%; $EC_{50}$, effective concentration 50% and RT, room temperature.

Anti-E2 monoclonal antibody 6F6 was acquired from Austral Biologicals (San Ramon, Calif.).

EXAMPLE 1

Development of a Unique HCV-E2/CD81 Binding Assay. This example demonstrates the binding of HCV-E2 to CD81 on Human T cells. The binding of HCV-E2 to CD81 has been reported by several groups (see, e.g. Allander, T., et al., "Hepatitis C virus envelope protein E2 binds to CD81 of tamarins" *Virology* 277:358–367, 2000). Often those studies involved interactions of purified recombinant proteins. We sought to confirm published findings and to test the ability of HCV-E2 to bind to CD81 expressed on living T cells. Various concentrations of recombinant HCV-E2 (Ala 384 to Lys 715 of the HCV polyprotein produced in CHO cells; Austral Biologicals) was incubated with Molt4 T cells and binding of HCV-E2 to the cells was detected with the anti-E2 monoclonal antibody 6F6 (Austral Biologicals) followed by flow cytometry (FIG. 1). HCV-E2 binding to Molt4 T cells is concentration dependent and easily detectable at concentrations as low as 0.3 μg/mL. This binding assay differs from the assay published by Wünschmann in that the published assay used whole virus and not recombinant HPV peptide. (Wünschmann, et al, "Characterization of Hepatitis C Virus (HCV) and HCV E2 Interactions with CD81 and the Low-Density Lipoprotein Receptor" *J. Virology* 74:10055–10062, 2000).

Figure 2:
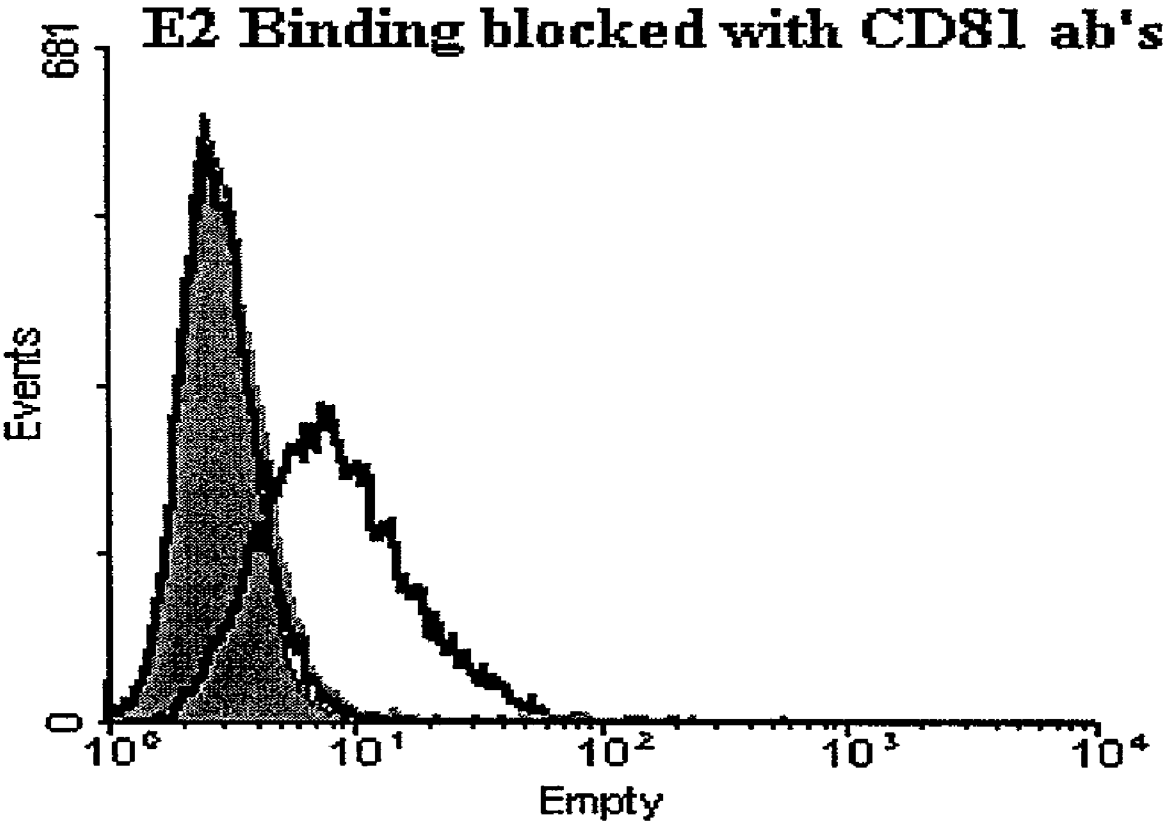
FIG. 2 shows the blockade of HCV-E2 binding to Molt4 T cells with anti-CD81 mAbs. T cells were pre-incubated with 5A6, JS81 (the 5A6 and JS81 histograms are superimposed on each other and are the left-most histograms) or control mAbs (right histogram) prior to incubation with HCV-E2 and detection by 6F6-biotin. The shaded (solid) histogram represents no E2 negative control.

In order to demonstrate that the binding of HCV-E2 to T cells was specifically mediated by CD81 we used antibodies to CD81 to block access of HCV-E2 to CD81. It was necessary to use a biotinylated 6F6 and streptavidin conjugated Alexa-488 in this experiment to avoid cross-reactivity of the blocking anti-CD81 with the detecting goat anti-mouse antibodies. Pre-incubation with 1 μg/mL 5A6 or JS81 (anti-CD81 mAbs), but not with control mAb, completely blocked HCV-E2 binding to Molt4 T cells (FIG. 2).

EXAMPLE 2

Synthesis of Oligomeric I45DCs. Overview of Protocols. This example demonstrates the synthesis of oligomeric I45DC compounds. In overview, the I45DCs are prepared from imidazole-4,5-dicarboxylic acid, compound 1, by the action of thionyl chloride to create an intermediate pyrazine (compound 2; Scheme 1).

Scheme 1.

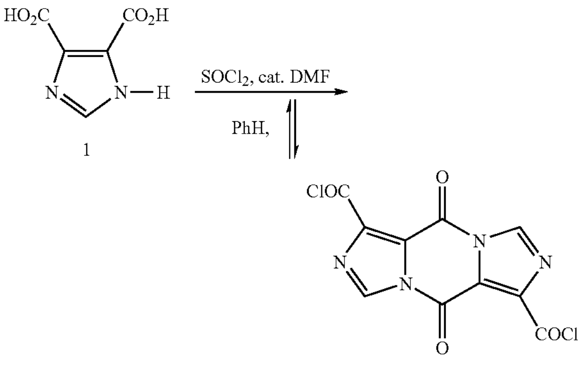

2, 94%

An important breakthrough for this invention was the inventor's empirical discovery that amino acid esters could be used to yield symmetric pyrazines in modest yields as shown in Scheme 2 and detailed in Table 1.

Scheme 2.

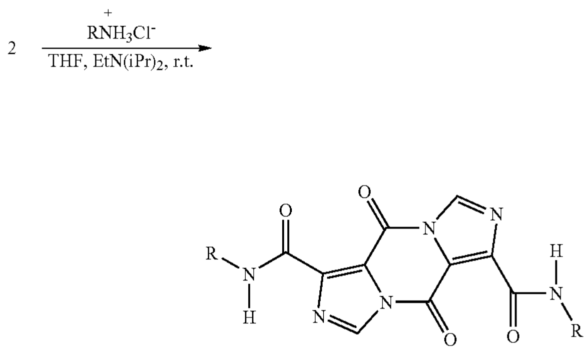

3-5

TABLE 1

Structures and yields of pyrazine amino acid ester examples.

| Compound | Substitution | Yield |
|---|---|---|
| 3 | R = (L)-PheOtBu | 40% |
| 4 | R = (L)-IleOtBu | 59% |
| 5 | R = (L)-ValOBzl | 69% |

Model oligomeric I45DC structures were prepared by opening symmetric pyrazines with a variety of diamines. For example, the reaction of pyrazines 3–5 with different diaminoalkanes gave good yields of the diimidazole compounds 6–9 as shown in Scheme 3 and as detailed in Table 2.

Scheme 3.

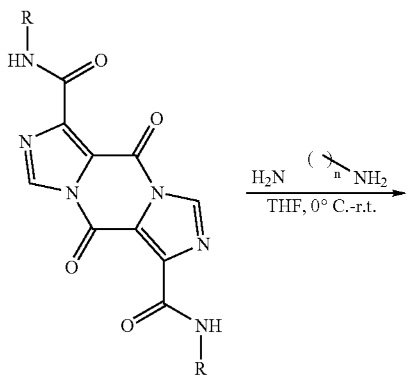

3-5

-continued

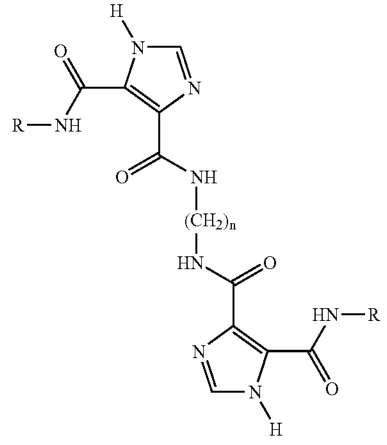

6-9

TABLE 2

| Structures and yields of model oligomers from the pyrazine amino acid ester examples. | | | |
|---|---|---|---|
| Cmpd | Pyrazine | Diamine | Yield |
| 6 | 3, PheOtBu | $H_2N$—$(CH_2)_6$—$NH_2$ | 73% |
| 7 | 4, IleOtBu | $H_2N$—$(CH_2)_6$—$NH_2$ | 47% |
| 8 | 5, ValOBzl | $H_2N$—$(CH_2)_2$—$NH_2$ | 69% |
| 9 | 5, ValOBzl | $H_2N$—$(CH_2)_4$—$NH_2$ | 67% |

In order to prepare model oligomers containing four amino acid side chains, we first linked Boc-(L)-PheOH to three different diamines by using the water-soluble carbodiimide, 1-3(3-dimethylaminopropyl)-3-ethylcarbodiimide hydrochloride (EDC), as the coupling reagent along with 1-hydroxybenzotriazole (HOBt) as shown in Scheme 4. The final compounds, 10–12, were obtained in good yields following the workup (Table 3).

Scheme 4.

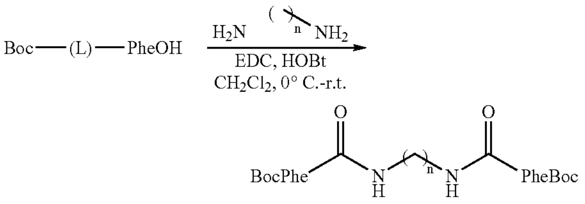

10-12

TABLE 3

| Structures and yields of Boc-protected phenylalanine-derivitized diamines. | | |
|---|---|---|
| Compound | Diamine | Yield |
| 10 | $H_2N$—$(CH_2)_2$—$NH_2$ | 23% |
| 11 | $H_2N$—$(CH_2)_3$—$NH_2$ | 52% |
| 12 | $H_2N$—$(CH_2)_4$—$NH_2$ | 73% |

The compounds 10–12 had each of their Boc protecting groups removed with trifluoroacetic acid (TFA). These compounds were added directly to an amino acid substituted pyrazine to give compounds 13–18 (Scheme 5). The details of these reactions are given in Table 4.

Scheme 5.

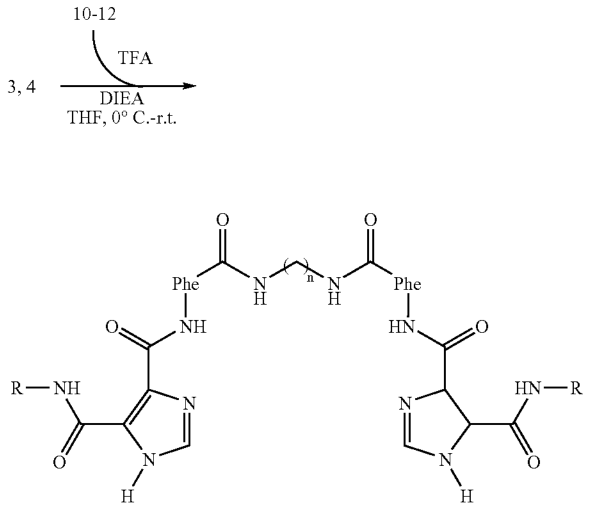

13-18

TABLE 4

| Structures and yields of oligomeric dimidazoles incorporating the Boc-protected phenylalanine-derivitized diamines. | | | |
|---|---|---|---|
| Cmpd | Pyrazine | n ($CH_2$) | Yield |
| 13 | 3, PheOtBu | 2 | 46% |
| 14 | 3, PheOtBu | 3 | 41% |
| 15 | 3, PheOtBu | 4 | 36% |
| 16 | 4, IleOtBu | 2 | 45% |
| 17 | 4, IleOtBu | 4 | 60% |
| 18 | 4, IleOtBu | 6 | 61% |

We also prepared compound 19 by adding N,N'-diethylethylenediamine to compound 5 as shown in Scheme 6. The resulting tertiary amide forces the intramolecular hydrogen bond to form in only one direction and thereby provides some control over the final conformation of the compound. This is the most active compound to date in the CD81 with HCV-E2 assay.

Scheme 6.

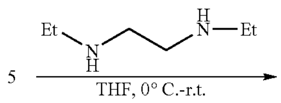

-continued

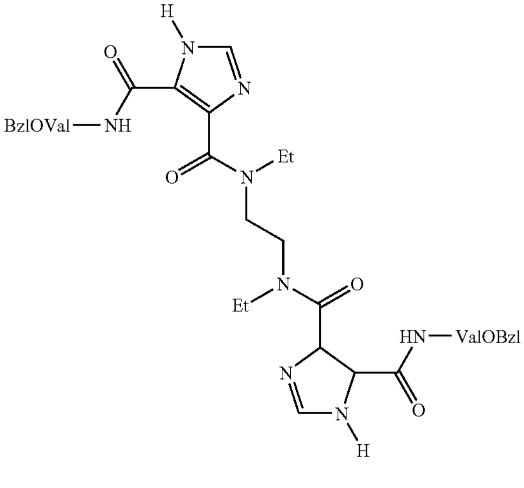

19, 31%

The oligomeric I45DC structures were characterized by $^1H$ and $^{13}C$ NMR spectroscopy as well as mass spectrometry.

Figure 7:
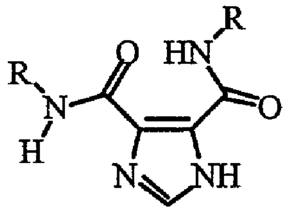
FIG. 7 shows the structures of several I45DC scaffold-based compounds of the present invention.
Figure 7:
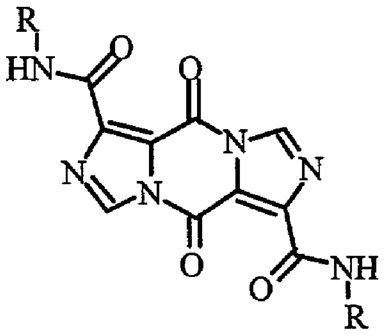

The detailed methods of synthesis for specific compounds, as well as their characterizations, are given below. The compound numbers in bold refer to the compounds in Schemes 1–6 and in FIG. 7.

Thus, modifications to the linker group, the amino acid side chain, and to the ester functionality have all been made to explore the impact of these changes on the observed ability to inhibit the HCV-E2 binding to CD81. The most active linker within the context of the valine benzyl ester containing I45DC (AL-2-140) was the N,N'-diethylethylenediamine, as AL-2-128, AL-2-130, AL-2-136, AL-2-222, and AL-2-243 were all less active in this binding assay. No change in binding inhibition was observed when the benzyl ester was changed to either a tert-butyl ester (AL-2-261) or ethyl ester (AL-2-263). An improvement in binding inhibition was obtained by changing the side chain from a valine residue to a leucine residue (AL-2-255) and the ester was shown to have some importance since the carboxylic acid analog (AL-2-269) was observed to have a reduced inhibitory activity in the binding assay.

I. 5,10-Dioxo-5H,10H-diimidazo{1,5-a:1',5'-d}pyrazine-1,6-dicarbonyl dichloride (compound 2).

To a dry roundbottom flask was added 21.0 g (135 mmol) of imidazole-4,5-dicarboxylic acid (compound 1) and 200 mL of benzene. To this stirred suspension was added dropwise 12.5 mL (162 mmol) dimethylformamide followed by 40 mL (550 mmoles) thionyl chloride. The solution was refluxed for 24 hours to yield a tan-colored solid in suspension. The solid was collected by vacuum filtration and washed with approximately 500 mL of benzene (until the filtrates were colorless). The solid was dried under a stream of $N_2$ gas to yield 20.5 g (97%) of (compound 2) as a yellow-tan powder. The sample was stored under argon. mp>200° C. (dec).

II. Symmetric imidazole-4,5-dicarboxylic acid disubstituted with amino acid esters.

General procedure. To a dry roundbottom flask under argon was added one mole equivalent of compound 2 and 25 mL dry tetrahydrofuran. To this stirred suspension at 0° C. was added four equivalents of the appropriate amino acid ester hydrochloride salt followed by six equivalents of diisopropylethylamine over 15 minutes. The solution was stirred at RT for 12 h before concentrating under vacuum to provide the crude product. The solid was dissolved in 25 mL dichloromethane and extracted with 10% citric acid, 1 M $NaHCO_3$, and brine. The organic layer was dried over $MgSO_4$ and stirred with approximately 200 mg of decolorizing carbon. The mixture was filtered and the filtrate was concentrated under vacuum to yield the final product.

Compound JR-1-74. 4,5-Bis{[(1,1-dimethylethoxy-S)-phenyl)alanyl]carbonyl}-1H-imidazole. Synthesized from 0.239 g of compound 2 to yield 0.767 g (89%) of compound JR-1-74 as a foam. $R_f$=0.70 (EtOAc:$CH_3OH$:$NH_4OH$, 95:4.5:0.5); $^1H$ NMR (DMSO-$d_6$) δ 13.36 (bs, 1H), 11.28 (bs, 1H), 8.51 (bs, 1H), 7.85 (s, 1H), 7.24 (bs, 10H) 4.51–4.78 (m, 2H), 2.93–3.36 (m, 4H), 1.36 (bs, 18H); $^{13}C$ NMR (DMSO-$d_6$) δ 169.9, 163.0, 157.6, 137.0, 136.5, 132.5, 129.3, 128.2, 126.6, 81.0, 54.6, 53.8, 37.5, 36.4, 27.5; FAB MS m/z=563 $[M+H]^+$; Anal. Calcd for $C_{31}H_{38}N_4O_6$: C, 66.17; H, 6.81; N, 9.96. Found: C, 66.16; H, 6.77; N, 9.60.

Compound JR-1-95. 4,5-Bis[(methoxy-(S)-phenylalanyl) carbonyl]-1H-imidazole. Synthesized from 0.400 g of compound 2 to yield 1.151 g (94%) of compound JR-1-95 as a foam. $R_f$=0.68 (EtOAc:$CH_3OH$:$NH_4OH$, 95:4.5:0.5). $^1H$ NMR ($CDCl_3$) δ 12.40 (bs, 1H), 11.65 (bs, 1H), 8.15 (bs, 1H), 7.52 (s, 1H), 7.26 (s, 10H), 4.71–5.15 (m, 2H), 3.73 (s, 6H), 3.10–3.40 (m, 4H); $^{13}C$ NMR (DMSO-$d_6$) δ 171.5, 163.1, 157.7, 137.2, 136.6, 132.5, 129.2, 128.3, 127.7, 126.7, 54.1, 53.2, 52.2, 52.0, 37.2, 36.0; MS (ES+): m/z=479 $[M+H]^+$; Anal. Calcd. for $C_{25}H_{26}N_4O_6$: C, 62.76; H, 5.48; N, 11.72. Found: C, 62.90; H, 5.41; N, 11.72.

Compound JR-1-81. 4,5-Bis[(methoxy-(S)-leucinyl)carbonyl]-1H-imidazole. Synthesized from 0.458 g of compound 2 to yield 1.112 g (93%) of compound JR-1-81 as a foam. $R_f$=0.66 (EtOAc:$CH_3OH$:$NH_4OH$, 95:4.5:0.5); $^1H$ NMR (DMSO-$d_6$) δ 10.03 (bs, 1H), 7.90 (s, 1H), 4.42–4.61 (m, 2H), 3.66 (s, 6H), 1.50–1.93 (m, 6H), 0.85–0.98 (m, 12H); $^{13}C$ NMR (DMSO-$d_6$) δ 172.4, 160.7, 136.6, 130.2, 52.0, 50.4, 24.4, 22.7, 21.2; FAB+MS m/z=411 $[M+H]^+$; Anal. Calcd. for $C_{19}H_{30}N_4O_6$: C, 55.60; H, 7.37; N, 13.65. Found: C, 55.51; H, 7.38; N, 13.56.

Compound JR-1-84. 4,5-Bis[(methoxy-(S)-valyl)carbonyl]-1H-imidazole. Synthesized from 0.492 g of compound 2 to yield 1.185 g (99%) of compound JR-1-84 as a foam. $R_f$=0.64 (EtOAc:$CH_3OH$:$NH_4OH$, 95:4.5:0.5). $^1H$ NMR (DMSO-$d_6$) δ 13.44 (bs, 1H), 11.14 (d, J=8.0 Hz, 1H), 8.37 (d, J=8.8 Hz, 1H), 7.92 (s, 1H), 4.36–4.49 (m, 2H), 3.68–3.69 (m, 6H), 2.09–2.28 (m, 2H), 0.91–1.01 (m, 12H); $^{13}C$ NMR (DMSO-$d_6$) δ 171.6, 171.4, 136.6, 158.0, 136.7, 132.3, 127.8, 57.7, 57.1, 52.1, 51.9, 19.0, 18.1, 17.6; FAB+MS m/z=383 $[M+H]^+$; Anal. Calcd. for $C_{17}H_{26}N_4O_6$: C, 53.40; H, 6.85; N, 14.65. Found: C, 53.53; H, 6.98; N, 14.56.

Compound JR-1-131. 4,5-Bis[(ethoxyglycyl)carbonyl]-1H-imidazole. Synthesized from 0.575 g of compound 2 to yield 0.403 g (33%) of compound JR-1-131 as a crystalline solid following silica gel chromatography and crystallization from $CH_2Cl_2$/hexanes. $R_f$=0.34 (EtOAc/hexanes, 7:3); $^1H$ NMR (DMSO-$d_6$) δ 13.40 (bs, 1H), 11.20 (bs, 1H), 9.00 (bs, 1H), 7.91 (s, 1H), 4.07–4.18 (m, 2H), 1.15–1.24 (m, 6H); $^{13}C$ NMR (DMSO-$d_6$) δ 169.5, 136.7, 60.59, 40.95, 14.08; ES+MS m/z=327 $[M+H]^+$; Anal. Calcd. for $C_{13}H_{18}N_4O_6$: C, 47.85; H, 5.56; N, 17.17. Found: C, 48.04; H, 5.35; N, 17.03.

Compound JR-1-99. 4,5-Bis {[(1,1-dimethylethoxy)glycyl]carbonyl}-1H-imidazole. Synthesized from 0.233 g of compound 2 to yield 0.512 g (89%) of compound JR-1-99 as a solid. $R_f$=0.66 (EtOAc:$CH_3OH$:$NH_4OH$, 95:4.5:0.5). $^1H$ NMR (DMSO-$d_6$) d 13.35 (bs, 1H), 11.20 (bs, 1H), 8.90 (bs, 1H), 7.89 (s, 1H), 3.96–3.99 (m, 4H), 1.42 (s, 18H); $^{13}C$ NMR (DMSO-$d_6$) d 168.5, 136.5, 80.9, 41.6, 27.7; FAB+ MS m/z=383 $[M+H]^+$; Anal. Calcd. for $C_{17}H_{26}N_4O_6$: C, 53.40; H, 6.85; N, 14.65. Found: C, 53.31; H, 6.82; N, 14.41.

Compound JR-1-91. 4,5-Bis[(methoxy-(S)-alanyl)carbonyl]-1H-imidazole. Synthesized from 0.576 g of compound 2 to yield 1.124 g (94%) of compound JR-1-91 as a foam. $R_f$=0.64 (EtOAc:$CH_3OH$:$NH_4OH$, 95:4.5:0.5). $^1H$ NMR (DMSO-$d_6$) d 10.1 (bs, 2H), 7.90 (s, 1H), 4.55 (p, 2H), 3.66 (s, 6H), 1.42 (d, 6H); $^{13}C$ NMR (DMSO-$d_6$) d 172.6, 160.4, 136.6, 130.3, 52.1, 47.7, 17.1; FAB+MS m/z=327 $[M+H]^+$; Anal. Calcd. for $C_{13}H_{18}N_4O_6$: C, 47.85; H, 5.56; N, 17.17. Found: C, 48.08; H, 5.58; N, 17.14.

III. 5,10-Dioxo-5H,10H-diimidazo{1,5-a:1',5'-d}pyrazine-1,6-dicarbonyl amino acid esters (compounds 3–5).

General Procedures.

Method A. (compound 3). To a dry roundbottom flask under argon was suspended 1.00 g (3.19 mmol) of compound 2 in 25 mL dry tetrahydrofuran. To this stirred solution at −78° C. was added two mole equivalents of amino acid ester hydrochloride followed by four mole equivalents of diisopropylethylamine over 15 min. The solution was held at −78° C. for 2 h and then stirred overnight at RT. Addition of two volume equivalents of water yielded a precipitate of crude product that was collected by vacuum filtration and dissolved in 50 mL of dichloromethane. This solution was dried over $MgSO_4$ and filtered. The final product precipitated upon the addition of hexanes and was collected by vacuum filtration.

Method B. (compounds 4,5) To a dry roundbottom flask under argon was suspended 1.00 g (3.19 mmol) of compound 2 in 25 mL dry dichloromethane. To this stirred solution at −78° C. was added two mole equivalents of the appropriate amino acid ester hydrochloride (or tosylate) salt followed by four mole equivalents of pyridine over 15 min. The solution was held at −78° C. for 30 min. and then stirred 1 h at RT. Solids were removed by filtration through celite and the filtrate was extracted against water (3×). The organic fraction was dried over $MgSO_4$, filtered, and concentrated. The residue was suspended in boiling ethyl acetate, stirred for 10 min, cooled to 0° C., and the product solid collected by vacuum filtration.

Compound 3. Synthesized from 0.918 g of compound 2 with L-phenylalanine tert-butyl ester hydrochloride via Method A to yield 0.790 g (40%) of compound 3 (JR-1-132) as a solid. $^1H$ NMR (DMSO-$d_6$) δ 9.02 (d, J=8.8 Hz, 2H), 9.00 (s, 2H), 7.20–7.33 (m, 10H), 4.64–4.72 (m, 4H), 3.12–3.19 (m, 4H), 1.37 (s, 18H); $^{13}C$ NMR ($CDCl_3$) δ 169.9, 158.7, 149.5, 143.8, 138.4, 136.9, 129.2, 128.3, 126.6, 120.6, 81.2, 54.4, 36.8, 27.5.

Compound 4. Synthesized from 0.917 g of compound 2 with L-isoleucine tert-butyl ester hydrochloride via Method A to yield 1.060 g (59%) of compound 4 (JR-1-133) as a solid. The presence of conformational isomers was evident in the $^1H$ NMR spectrum. $^1H$ NMR (DMSO-$d_6$) δ 9.02–9.08 (m, 2H), 4.36–4.48 (m, 2H), 1.91–1.98 (m, 2H), 1.42–1.46 (m, 18H), 1.26–1.37 (m, 4H), 0.88–1.00 (m, 12H); $^{13}C$ NMR ($CDCl_3$) δ 169.9, 158.8, 150.4, 144.2, 138.9, 120.3, 81.3, 57.1, 36.9, 27.7, 24.9, 15.5, 11.4.

Compound 5. Synthesized from 2.039 g of compound 2 with L-valine benzyl ester hydrochloride via Method B to yield 3.118 g (73%) of compound 5 (AL-2-220) as a solid. $^1H$ NMR ($CDCl_3$) δ 8.78 (d, J=8.8 Hz, 2H), 8.65 (s, 2H), 7.33–7.38 (m, 10H), 5.16–5.25 (m, 4H), 4.86–4.89 (m, 2H), 2.34–2.38 (m, 2H), 0.98–1.02 (m, 12H; $^{13}C$ NMR ($CDCl_3$) δ 171.5, 158.1, 149.8, 147.1, 138.9, 135.5, 128.9, 128.8, 119.2, 67.6, 58.1, 31.6, 19.4, 17.9.

Compound AL-2-257. Synthesized from 1.017 g of compound 2 via Method B to yield 1.342 g (77%) of compound AL-2-257 as a solid. $^1H$ NMR ($CDCl_3$) δ 8.71 (s, 2H), 8.69 (s, 2H), 4.82–4.85 (m, 4H), 4.22–4.30 (m, 4H), 2.33–2.41 (m, 2H), 1.30–1.34 (m, 6H), 1.04–1.06 (m, 12H); $^{13}C$ NMR ($CDCl_3$) δ 171.4, 157.9, 149.5, 147.1, 138.8, 118.9, 61.7, 57.9, 31.5, 19.2, 17.9, 14.4; FAB MS m/z 531 $[M+H]^+$.

Compound AL-2-259. Synthesized from 1.858 g of compound 2 via Method B to yield 2.769 g (80%) of compound AL-2-259 as a solid. $^1H$ NMR ($CDCl^3$) δ 8.76 (d, J=8.8 Hz, 2H), 8.70 (s, 2H), 4.76 (dd, J=8.8 Hz, J=8.8 Hz, m, 2H), 2.32–2.36 (m, 2H), 1.50 (s, 18H), 1.04 (d, J=6.8 Hz, 12H); $^{13}C$ NMR ($CDCl_3$) δ 170.8, 158.0, 149.7, 147.5, 139.0, 119.0, 82.7, 58.4, 31.9, 28.4, 19.4, 18.0.

Compound AL-2-239. Synthesized from 0.975 g of compound 2 via Method B to yield 1.144 g (54%) of compound AL-2-239 as a solid. $^1H$ NMR ($CDCl_3$) δ 8.65 (s, 2H), 8.56 (d, J=8.4 Hz, 2H), 7.37 (bs, 10H), 5.21 (s, 4H), 4.92–4.97 (m, 2H), 1.73–1.85(m, 6H), 0.96–0.99 (m, 12H); $^{13}C$ NMR ($CDCl_3$) δ 172.5, 157.9, 149.4, 147.1, 138.8, 135.6, 129.0, 128.8, 128.7, 119.2, 67.7, 51.8, 41.7, 25.3, 23.2, 22.3; FAB MS m/z 683 $[M+H]^+$.

IV. Amino acid ester-substituted bis-imidazoles (compounds 6, 8, 9, 13, 14, 16, 17, 19).

General Procedures.

Method C. (Compound 8). To a dry roundbottom flask under argon was added one mole equivalent of an amino acid ester-substituted pyrazine in 5 mL dry dichloromethane. To this stirred solution at RT was added one mole equivalent of the appropriate aliphatic diamine. The solution was stirred for 2 h at RT before adding 20 mL of methanol. The solution was concentrated to approximately one-third the volume and the resulting precipitate collected by vacuum filtration. The solid was further dried under high vacuum.

Method D. (Compound 9) To a dry roundbottom flask under argon was added one mole equivalent of an amino acid ester-substituted pyrazine in 5 mL dry dichloromethane. To this stirred solution at RT was added one mole equivalent of the appropriate aliphatic diamine. The solution was stirred for 2 h before extracting with 0.1 M HCl, water, 0.1 M NaOH, and water. The organic layer was dried over $MgSO_4$, filtered, and concentrated under vacuum to yield a viscous oil that solidified under high vacuum.

Method E. (Compound 6) To a dry roundbottom flask under argon was added one mole equivalent of an amino acid ester-substituted pyrazine in 5 mL dry dichloromethane. To this stirred solution at RT was added one mole equivalent of the appropriate aliphatic diamine. The solution was stirred for 2 h before concentration under vacuum to a crude solid that was redissolved in 10 mL of boiling methanol. Addition of 2 mL of water was followed by cooling to RT with stirring. After 3 h, the precipitated solids were collected, washed with cold methanol and the process of dissolving in hot MeOH, adding water, and then stirring at RT was repeated. The final precipitate was washed with cold methanol and dried under vacuum.

Method F. (Compound 19) To a dry roundbottom flask under argon was added one mole equivalent of an amino acid ester-substituted pyrazine in 5 mL dry dichloromethane. To this stirred solution at −78° C. was added one mole equivalent of the appropriate aliphatic diamine. The solution was stirred for 4 h at RT. The solution was extracted with 10% citric acid, 1 M $NaHCO_3$, and brine, dried over $MgSO_4$, filtered, and concentrated under vacuum to yield a crude product that was further purified by either precipitation or column chromatography.

Method G. (Compound AL-2-136) To a dry roundbottom flask under argon was added one mole equivalent of an amino acid ester-substituted pyrazine in 5 mL dry dichloromethane. To this stirred solution at RT was added one mole equivalent of the appropriate aliphatic diamine. The solution was stirred for 2 h at RT before the solids were collected by filtration and washed with a 2 mL portion of dichloromethane. To the filtrate was added an equal volume of hexane to further precipitate the product solid.

Method H. (Compound AL-2-243) To a dry roundbottom flask under nitrogen was added one mole equivalent of an amino acid substituted pyrazine in 2 mL dry dichloromethane/tetrahydrofuran (3:1). To this stirred solution at RT was added one mole equivalent of ethylene glycol. The solution was refluxed for 20 h before the solids were collected by filtration and washed with a 2 mL portion of dichloromethane before drying under vacuum.

Method I. (Compounds 13, 14, 16, 17) To a dry roundbottom flask under argon was added the appropriate deprotected diamine-linked diamino acid trifluoroacetate salt in 25 mL dry tetrahydrofuran. To this stirred solution was added one mole equivalent of the appropriate amino acid substituted pyrazine followed by cooling to −78° C. and the dropwise addition of a tetrahydrofuran solution containing two mole equivalents of diisopropylethylamine. The ice bath was removed after 5 min. and the solution was stirred for 18 h at RT. The tetrahydrofuran was removed under vacuum and the residues were redissolved in ethyl acetate. The solution was extracted with 1 M HCl, 1 M NaOH, and brine, dried over $MgSO_4$, filtered, and concentrated under vacuum to yield the desired product.

Compound 8. Synthesized from 0.101 g of compound 5 via Method C to yield 52 mg (47%) of compound 8 (AL-2-125) as a solid. $^1H$ NMR (DMSO-$d_6$) δ 13.24 (bs, 2H), 11.54 (bs, 2H), 8.85 (bs, 2H), 7.83 (s, 2H), 7.29–7.38 (m, 10H), 5.12–5.19 (s, 4H), 4.40–4.43 (m, 2H), 3.48–3.56 (m, 4H), 2.14–2.22 (m, 2H), 0.89–0.91 (d, J=7.2 Hz, 12H); The carbonyl resonances were broad in the $^{13}C$ NMR spectra. The ethylenediamine signals were masked and unobserved by the DMSO-$d_6$ signals. $^{13}C$ NMR (DMSO-$d_6$) δ 171.0, 163.7, 158.4, 136.2, 135.9, 133.2, 128.4, 128.0, 127.9, 65.9, 57.7, 30.0, 19.0, 17.6; FAB MS m/z 715 $[M+H]^+$.

Compound 9. Synthesized from 0.102 g of compound 5 via Method D to yield 82 mg (69%) of compound 9 (AL-2-127) as a solid. The imidazole and amide NHs were broad and conformationally averaged in the $^1H$ NMR spectrum. $^1H$ NMR ($CDCl_3$) δ 7.29–7.39 (m, 12H), 5.16–5.28 (m, 4H), 4.61–4.78 (m, 2H), 3.46–3.60 (m, 4H), 2.33–2.41 (m, 2H), 1.77–1.84 (m, 4H), 0.98–1.04 (m, 12H); The carbonyl resonances were broad in the $^{13}C$ NMR spectra. $^{13}C$ NMR ($CDCl_3$) δ 171.3, ~160, 135.8, 128.9, 128.7, 67.3, 58.5, 39.8, 31.3, 27.2, 19.6, 18.3; FAB MS m/z 743 $[M+H]^+$.

Compound 6. Synthesized from 0.101 g of compound 5 via Method E to yield 87 mg (73%) of compound 6 (AL-2-132) as a solid. $^1H$ NMR ($CDCl_3$) δ 13.24 (bs, 2H), 11.66 (bs, 2H), 8.63 (bs, 2H), 7.81 (s, 2H), 7.18–7.24 (m, 10H), 4.58–4.61 (m, 2H), 3.28–3.32 (m, 4H), 3.08–3.16 (m, 4H), 1.46–1.60 (m, 4H), 1.32 (s, 18H); The carbonyl resonances were unobserved in the $^{13}C$ NMR spectra. $^{13}C$ NMR (DMSO-$d_6$) δ 170.2, 136.7, 129.8, 128.8, 127.3, 40.2, 38.7, 29.1, 28.3, 26.7; FAB MS m/z 800 $[M+H]^+$.

Compound 13. Synthesized from 0.099 g of deprotected diamine-linked diamino acid trifluoroacetate salt and 0.109 g of compound 3 via Method I to yield 77 mg (46%) of compound 13 (JR-1-155a) as an oil. There was evidence of conformational isomers in the $^1H$ NMR spectrum. $^1H$ NMR (DMSO-$d_6$) δ 12.80 (bs, 2H), 10.50 (bs, 2H), 8.27 (bs, 2H), 7.81 (s, 2H), 7.16–7.24 (m, 20H), 4.63–4.69 (m, 4H), 3.60–3.80 (m, 4H), 2.93–3.20 (m, 8H), 1.34 (s, 18H).

Compound 14. Synthesized from 0.100 g of deprotected diamine-linked diamino acid trifluoroacetate salt and 0.109 g of compound 3 via Method I to yield 69 mg (41%) of compound 14 (JR-1-155b) as an oil. There was evidence of conformational isomers in the $^1H$ NMR spectrum. $^1H$ NMR (DMSO-$d_6$) δ 13.30 (bs, 1H), 13.22 (bs, 1H), 11.30–11.31 (m, 1H), 11.12–11.13 (m, 1H), 8.41–8.43 (m, 1H), 8.33–8.35 (m, 1H), 8.18–8.22 (m, 1H), 8.05–8.10 (m, 1H), 7.80–7.83 (m, 1H), 7.68–7.70 (m, 1H), 7.10–7.27 (m, 20H), 4.74–4.75 (m, 2H), 4.56–4.59 (m, 2H), 4.14 (bs, 2H), 3.20–3.22 (m, 2H), 2.78–3.20 (m, 8H), 1.20–1.50 (m, 18H), 0.85–0.89 (m, 2H).

Compound 16. Synthesized from 0.045 g of deprotected diamine-linked diamino acid trifluoroacetate salt and 0.045 g of compound 3 via Method I to yield 34 mg (45%) of compound 16 (JR-1-152) as an oil. There was evidence of conformational isomers in the $^1H$ NMR spectrum. $^1H$ NMR (DMSO-$d_6$) δ 13.28 (bs, 2H), 11.11–11.13 (m, 2H), 8.10–8.40 (m, 4H), 7.82 (s, 2H), 7.14–7.25 (m, 10H), 4.75–4.77 (m, 1H), 4.45–4.60(m, 2H), 4.29–4.32 (m, 1H), 2.80–3.20 (m, 8H), 1.80–1.90 (m, 2H), 1.38–1.48 (m, 18H), 1.18–1.30 (m, 4H), 0.85–0.96 (m, 12H).

Compound 17. Synthesized from 0.096 g of deprotected diamine-linked diamino acid trifluoroacetate salt and 0.096 g of compound 3 via Method I to yield 102 mg (61%) of compound 17 (JR-1-154) as an oil. There was evidence of conformational isomers in the $^1H$ NMR spectrum. $^1H$ NMR (DMSO-$d_6$) δ 13.29 (bs, 2H), 11.13 (bs, 2H), 8.10–8.40 (m, 4H), 7.83 (s, 2H), 7.10–7.30 (m, 10H), 4.60–4.80 (m, 2H), 4.30–4.55 (m, 2H), 2.95–3.15 (m, 8H), 1.80–2.00 (m, 2H), 1.20–1.50 (m, 28H), 0.90 (bs, 12H).

Compound 19. Synthesized from 0.256 g of compound 5 via Method F to yield 148 mg (s, 2H), 7.86 (s, 2H), 7.25–7.36 (m, 10H), 5.13–5.19 (m, 4H), 4.41–4.45 (m, 2H), 3.94–4.00 (m, 1H), 3.61–3.81 (m, 3H), 3.49–3.56 (m, 4H), 2.17–2.21 (m, 2H), 1.12–1.26 (m, 4H), 0.92–0.96 (m, 12H); The carbonyl resonances and the ethylenediamine resonances show multiple signals in the $^{13}C$ NMR spectra. $^{13}C$ NMR ($CDCl_3$) δ 171.0, 165.5, 165.4, 165.2, 165.1, 158.8, 158.7, 135.9, 134.4, 134.3, 128.4, 128.1, 128.0, 66.0, 57.6, 47.2, 45.6, 45.2, 44.7, 44.4, 43.6, 42.1, 41.6, 30.0, 29.9, 19.0, 17.4, 17.2, 14.3, 14.2.

Compound AL-2-128. Synthesized from 0.106 g of compound 5 via Method D to yield 85 mg (71%) of compound AL-2-128 as an oil. $^1H$ NMR (DMSO-$d_6$) δ 13.29 (bs, 2H), 11.59 (bs, 2H), 8.89 (bs, 2H), 7.85 (s, 2H), 7.28–7.37 (m, 10H), 5.12–5.33 (m, 4H), 4.42–4.44 (m, 2H), 3.33–3.36 (m, 4H), 2.17–2.23 (m, 2H), 1.73–1.80 (m, 2H), 0.93 (d, J=6.8 Hz, 12H); The carbonyl resonances were broad in the $^{13}C$ NMR spectra. $^{13}C$ NMR ($CDCl_3$) δ 171.0, 162.9, 158.9, 136.3, 135.9, 132.9, 128.4, 128.1, 127.9, 65.9, 57.8, 36.1, 30.0, 29.2, 19.1, 17.7; FAB MS m/z 729 $[M+H]^+$.

Compound AL-2-130. Synthesized from 0.100 g of compound 5 via Method C to yield 79 mg (67%) of compound AL-2-130 as a solid. $^1H$ NMR (DMSO-$d_6$) δ 13.22 (bs, 2H), 11.62 (bs, 2H), 8.68 (bs, 2H), 7.84 (s, 2H), 7.29–7.38 (m, 10H), 5.12–5.19 (m, 4H), 4.42–4.45 (m, 2H), 3.26–3.44 (m, 4H), 2.22–2.33 (m, 2H), 1.50–1.52 (m, 4H), 1.23–1.32 (m, 4H), 0.93 (d, J=6.8 Hz, 12H); The carbonyl resonances were broad in the $^{13}C$ NMR spectra. $^{13}C$ NMR ($CDCl_3$) δ 171.0, ~160, 136.3, 135.9, 128.4, 128.1, 127.9, 66.0, 57.7, 57.6, 30.0, 28.9, 26.1, 19.0, 17.7; FAB MS m/z 771 $[M+H]^+$.

Compound AL-2-136. Synthesized from 0.109 g of compound 5 via Method G to yield 73 mg (49%) of compound AL-2-130 as a solid. $^1$H NMR (DMSO-$d_6$) δ 12.69 (bs, 2H), 9.19 (bs, 2H), 7.65 (s, 2H), 7.29–7.39 (m, 10H), 5.11–5.14 (m, 4H), 4.36–4.53 (m, 2H), 2.84–2.89 (m, 8H), 2.16–2.33 (m, 2H), 1.53–1.58 (m, 8H), 1.24–1.33 (m, 8H), 0.93–0.95 (m, 12H), 0.84 (t, J=7.2 Hz, 6H); The carbonyl resonances were broad in the $^{13}$C NMR spectra. $^{13}$C NMR (DMSO-$d_6$) δ 171.5, ~162, ~161, 136.1, 135.0, 128.4, 128.0, 127.8, 65.6, 58.2, 46.5, 29.9, 27.5, 25.3, 25.1, 19.3, 19.2, 17.9, 13.5; FAB MS m/z 453 $[M+H+Na]+^2$.

Compound AL-2-222. Synthesized from 1.028 g of compound 5 via a modified Method D to yield 0.983 g (85%) of compound AL-2-222 as a solid. The modification was to suspend the crude solid from extraction in boiling ethyl acetate for 30 min, cooling to 0° C., filtering the solid, and washing the solid with cold ethyl acetate before drying under vacuum. $^1$H NMR ($CDCl_3$) δ 13.33 (bs, 2H), 10.25 (bs, 2H), 7.85–7.89 (m, 2H), 7.32–7.36 (m, 10H), 5.15–5.19 (m, 4H), 4.41–4.43 (m, 2H), 3.71–4.03 (m, 8H), 2.11–2.19 (m, 2H), 0.92 (bs, 12H); $^{13}$C NMR ($CDCl_3$) δ 171.1, 163.7, 159.5, 135.5, 134.7, 133.6, 129.5, 128.5, 128.3, 128.2, 66.8, 60.4, 58.7, 52.9, 48.0, 47.3, 43.7, 43.0, 30.6, 19.3, 17.8, 14.1; FAB MS m/z 741 $[M+H]^+$.

Compound AL-2-243. Synthesized from compound 5 via Method H to yield 0.069 g (49%) of compound AL-2-243 as a solid. $^1$H NMR ($CDCl_3$) δ 13.53 (bs, 2H), 10.17 (bs, 2H), 7.85 (m, 2H), 7.31–7.36 (m, 10H), 5.13–5.20 (m, 4H), 4.61–4.68 (m, 4H), 4.32–4.34 (m, 2H), 2.13–2.21 (m, 2H), 0.86–0.90 (m, 12H); $^{13}$C NMR ($CDCl_3$) δ 170.7 165.1, 157.7, 137.3, 135.8, 131.0, 129.5, 128.4, 128.1, 128.0, 66.1, 63.3, 57.6, 30.0, 25.1, 21.8, 18.9, 17.4, 10.9; FAB MS m/z 717 $[M+H]^+$.

Compound AL-2-255. Synthesized from 0.501 g of compound AL-2-239 via a modified version of Method F to yield 0.344 g (59%) of compound AL-2-255 as a solid. The modification was to stir the solution at −60° C. for 2 hours and then allowing to warm to RT prior to extraction. The crude product was purified by silica gel column chromatography with dichloromethane/methanol (98.5:1.5) as the eluant. $^1$H NMR (DMSO-$d_6$) δ 13.35 (bs, 2H), 10.24 (bs, 2H), 7.82–7.84 (m, 2H), 7.13–7.37 (m, 10H), 5.12–5.16 (m, 4H), 4.49–4.58 (m, 2H), 3.40–3.68 (m, 8H), 1.58–1.74 (m, 6H), 1.09–1.17 (m, 6H), 0.85–0.90 (m, 12H); The carbonyl resonances were broad in the $^{13}$C NMR spectra. $^{13}$C NMR (DMSO-$d_6$) δ 171.9, 171.8, 162.5, 158.6, 135.9, 128.4, 128.0, 127.8, 127.7, 66.0, 50.6, 47.0, 45.5, 44.7, 44.3, 24.4, 22.6, 21.5, 14.1, 12.3; FAB MS m/z 800 $[M+H]^+$.

Compound AL-2-261. Synthesized from 0.504 g of compound AL-2-259 via a modified version of Method F to yield 0.256 g (42%) of compound AL-2-261 as a solid. The modification was to stir the solution at −60° C. for 2 hours and then allowing to warm to RT prior to extraction. The crude product was purified by silica gel column chromatography with dichloromethane/methanol (98.5:1.5) as the eluant. Conformational isomers were evident in the $^1$H NMR spectrum. $^1$H NMR (DMSO-$d_6$) δ 13.30 (bs, 2H), 10.14–10.20 (m 2H), 7.83–7.88 (m, 2H), 4.23–4.26 (m, 2H), 3.47–3.99 (m, 8H), 2.12–2.15 (m, 2H), 1.40–1.41 (m, 18H), 1.15–1.29 (m, 6H), 0.92–0.97 (m, 12H); $^{13}$C NMR (DMSO-$d_6$) δ 170.1, 165.2, 158.6, 135.7, 134.2, 128.4, 80.7, 58.0, 47.2, 44.4, 30.1, 29.1, 27.6, 26.1, 19.2, 17.4, 14.2, 12.2; FAB MS m/z 703 $[M+H]^+$.

Compound AL-2-263. Synthesized from 0.504 g of compound AL-2-257 via a modified version of Method F to yield 0.173 g (28%) of compound AL-2-263 as a solid. The modification was to stir the solution at −60° C. for 2 hours and then allowing to warm to RT prior to extraction. The crude product was purified by silica gel column chromatography with dichloromethane/methanol (98.5:1.5) as the eluant. $^1$H NMR (DMSO-$d_6$) δ 13.27 (bs, 2H), 10.23 (bs, 2H), 7.82–7.84 (m, 2H), 4.32–4.35 (m, 2H), 4.09–4.14 (m, 4H), 3.47–3.94 (m, 8H), 2.11–2.18 (m, 2H), 1.13–1.25 (m, 6H), 0.93–0.95 (m, 12H); The carbonyl resonances were broad in the $^{13}$C NMR spectra. $^{13}$C NMR (DMSO-$d_6$) δ 171.7, 164.9, 159.8, 135.0, 129.5, 128.9, 61.5, 59.1, 46.0, 42.7, 30.9, 19.7, 18.2, 14.6, 12.9; FAB MS m/z 647 $[M+H]^+$.

Hydrogenation of compound AL-2-255 to produce compound AL-2-269. Synthesized from 0.042 g of compound AL-2-255 by catalytic hydrogenation. To a solution of compound AL-2-255 in 10 mL of methanol was added 40 mg of a 10% Pd/C catalyst under nitrogen. The mixture was shaken with 20 psi $H_2$ for 1 h. The solution was filtered through celite to remove the catalyst and the methanol was removed under vacuum to quantitatively yield AL-2-266 as an oil. $^1$H NMR (DMSO-$d_6$) δ 13.08 (bs, 2H), 12.72 (bs, 2H), 19.92 (bs, 2H), 7.81–7.88 (m, 2H), 4.37–4.45 (m, 2H), 3.17–3.88 (m, 8H), 1.60 (bs, 6H), 1.11–1.21 (m, 6H), 0.87–0.90 (m, 12H).

V. Synthesis of Diamine-Linked Diamino Acids. (Compounds 10-12; JR-1-124, JR-1-137, and JR-1-144, Respectively).

General Method. To a dry roundbottom flask under argon was added a Boc-protected amino acid in 5 mL dry dichloromethane. To this stirred solution at 0° C. was added a water-soluble carbodiimide all at once followed by the dropwise addition of the liquid diamine. The solution was stirred for 12 h at RT before extracting with 10% citric acid, 1 M $NaHCO_3$, and brine. The organic fraction was dried over $MgSO_4$, filtered, and concentrated under vacuum to yield a crude product that was used without further purification.

Compound 10. Synthesized from 4.782 g of Boc-(S)-phenylalanine and 0.60 mL of ethylenediamine by the general method to yield 1.143 g (23%) of crude compound 10. $^1$H NMR ($CDCl_3$) δ 7.12–7.27 (m, 10H), 5.90–6.08 (bs, 2H), 5.15–5.25 (m, 2H), 4.10–4.20 (m, 2H), 2.88–3.20 (m, 8H), 1.25–1.45 (m, 18H); $^{13}$C NMR ($CDCl_3$) d 172.2, 155.5, 137.0, 129.7, 128.9, 127.2, 80.5, 56.4, 39.3, 28.6.

Compound 11. Synthesized from 2.000 g of Boc-(S)-phenylalanine and 0.32 mL of 1,3-propanediamine by the general method to yield 1.121 g (52%) of crude compound 11. $^1$H NMR (DMSO-$d_6$) δ 7.85 (bs, 2H), 7.15–7.30 (m, 10H), 6.85–6.95 (m, 2H), 4.02–4.12 (m, 4H), 2.70–3.05 (m, 6H), 1.40–1.50 (m, 2H), 1.20–1.33 (m, 18H), 1.00–1.10 (m, 2H); $^{13}$C NMR ($CDCl_3$) δ 172.1, 155.9, 136.9, 129.6, 128.9, 127.1, 80.5, 77.5, 56.4, 38.7, 36.6, 28.5.

Compound 12. Synthesized from 2.020 g of Boc-(S)-phenylalanine and 0.38 mL of 1,4-butanediamine by the general method to yield 1.594 g (73%) of crude compound 12. $^1$H NMR ($CDCl_3$) δ 7.20–7.30 (m, 10H), 6.45–6.55 (bs, 2H), 5.25–5.45 (m, 2H), 4.30–4.45 (m, 2H), 3.15–3.25 (m, 2H), 2.85–3.15 (m, 6H), 1.15–1.45 (m, 22H); $^{13}$C NMR ($CDCl_3$) δ 171.9, 155.9, 137.1, 129.6, 128.8, 127.0, 80.4, 77.5, 56.3, 39.0, 28.5, 26.3.

VI. Deprotection of the Diamine-Linked Diamino Acids.

General Method. To a dry roundbottom flask under argon was added a diamine-linked diamino acid in dry dichloromethane. To this stirred solution at 0° C. was added trifluoroacetic acid dropwise. The solution was stirred for 2 h at RT before evaporating the solvent and acid under vacuum. The residues were dissolved in dichloromethane and concentrated under vacuum three separate times to yield an oil that was used without further purification.

EXAMPLE 3

Effect of I45DCs on HCV-E2 binding to CD81 on T cells. This example demonstrates the effectiveness of the I45DC scaffold-based compounds of the present invention in inhibiting HCV-E2 binding to CD81 on Human T cells. Binding was measured by using the novel and sensitive method of the present invention for the detection of binding between the HCV envelope protein E2 and its cellular receptor CD81 on living human T cells. This experimental approach was employed in the evaluation of a series of newly synthesized I45DCs.

Figure 5:
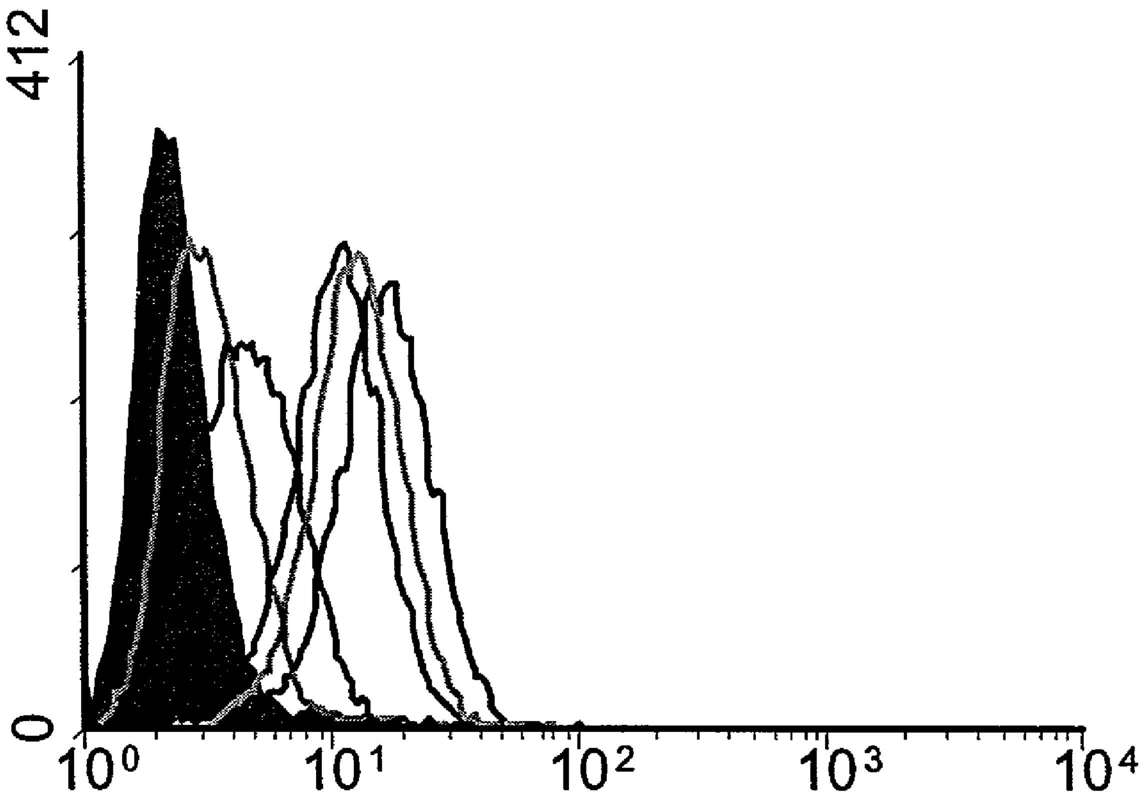
FIG. 5 shows flow cytometry data illustrating HCV-E2 binding to Molt4 cells in the presence of varying concentrations of compound 19. Concentrations of compound 19 were 250, 125, 62.5, 31.25, and 0 μM left to right, respectively. The shaded (solid) histogram represents no E2 negative control.

Two compounds, 8 and 19, showed bioactivity in the sub-millimolar range in the HCV-E2 binding assay. HCV-E2 was pre-incubated with or without 500 mM of the indicated compound for 30 minutes at 37° C. prior to addition of HCV-E2 to Molt4 cells and detection as described above. Compound 20 is an amino acid ester substituted symmetric I45DC which proved inactive in this assay and is shown as a negative control. The approximate $EC_{50}$ of 19 was determined by conducting the same type of experiment in the presence of a 1:2 titration of 19 from 250 mM to 31.25 mM (FIG. 5).

Figure 6:
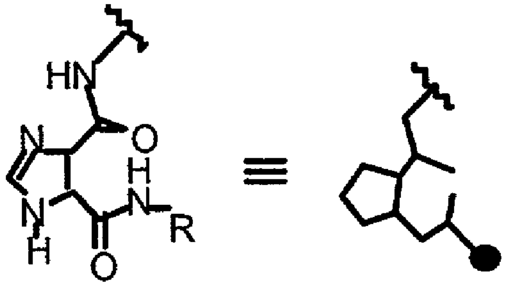
FIGS. 6A, 6B and 6C show some conformational isomers possible for the model oligomers containing two I45DCs. (A) shows a shorthand representation of an I45DC scaffold. (B) shows conformational isomers with the intramolecular hydrogen bonds pointed toward the linker (left) and away from the linker (right). The top and bottom representations indicate the flexibility that could be expected in the linker group. (C) shows conformation isomers with the intramolecular hydrogen bonds pointed in opposite directions away from and toward the linker group. The squiggly line "∿" represents the linker.
Figure 6:
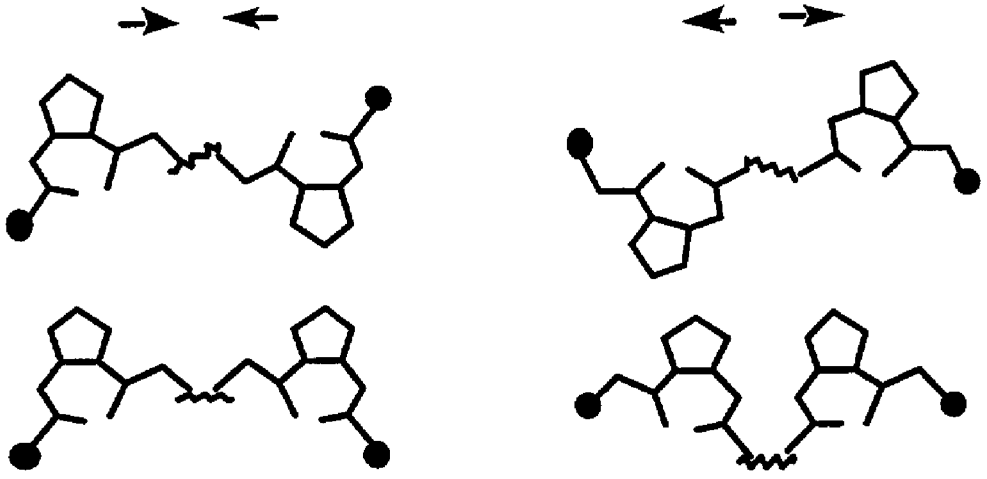
Figure 6:
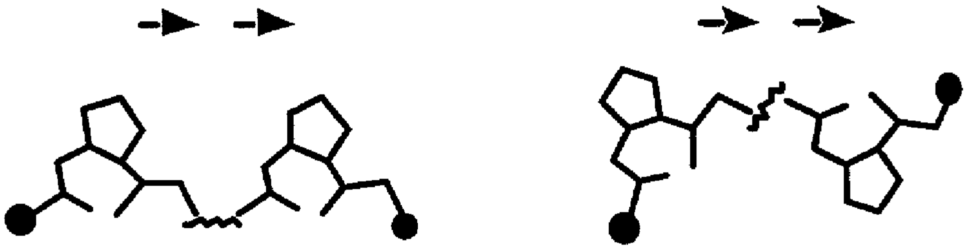

Some of these oligomeric I45DC structures show the presence of multiple conformational isomers, as the intramolecular hydrogen bonds that form yield different symmetric and dissymmetric conformations (FIG. 6). The most bioactive I45DC oligomer discovered to date controls the direction of the intramolecular hydrogen bond (FIG. 6C) by the presence of a secondary amide on one side of the imidazole formed with an amino acid and a tertiary amide on the other side of the imidazole formed by reaction with a secondary amine. The I45DCs that form multiple conformations were not as active in the CD81 with HCV-E2 binding assay, presumably because multiple conformations reduce the effective concentration of the important conformer in solution. The improved activity in the assay may be wholly or partially connected to the comparatively limited conformations available for compounds such as 19 (Michnick, S. W. "Exploring Protein Interactions by Interaction-Induced Folding of Proteins from Complementary Peptide Fragments" *Curr. Opin. Struct. Biol.* 11:472–477, 2001) and additional analogs currently in development have been designed to test this hypothesis.

From the foregoing it is evident that the present invention contemplates novel I45DC scaffold-based compounds, novel methods of synthesis of I45DC scaffold-based compounds as well as novel methods of drug screening and novel methods of treatment of Hepatitis C virus infection with I45DC scaffold-based compounds.

We claim:

1. A compound produced by reacting an imidazole-4,5-dicarboxylic acid scaffold with N,N'-diethylethylenediamine.

2. A compound selected from the group consisting of AL-2-128, AL-2-130, AL-2-136, AL-2-222, AL-2-243, AL-2-255, AL-2-261, and AL-2-263.

3. The compound of claim 1, wherein said compound is AL-2-140 .

* * * * *